(12) United States Patent
Otis et al.

(10) Patent No.: US 9,814,387 B2
(45) Date of Patent: Nov. 14, 2017

(54) DEVICE IDENTIFICATION

(71) Applicant: Verily Life Sciences LLC, Mountain View, CA (US)

(72) Inventors: Brian Otis, Sunnyvale, CA (US); Daniel Yeager, Berkeley, CA (US); Andrew Nelson, Richmond, CA (US)

(73) Assignee: Verily Life Sciences, LLC, South San Francisco, CA (US)

( * ) Notice: Subject to any disclaimer, the term of this patent is extended or adjusted under 35 U.S.C. 154(b) by 258 days.

(21) Appl. No.: 13/930,513

(22) Filed: Jun. 28, 2013

(65) Prior Publication Data

US 2015/0002270 A1 Jan. 1, 2015

(51) Int. Cl.
*G06K 7/10* (2006.01)
*A61B 5/00* (2006.01)
(Continued)

(52) U.S. Cl.
CPC .......... *A61B 5/0002* (2013.01); *A61B 5/1477* (2013.01); *A61B 5/14532* (2013.01);
(Continued)

(58) Field of Classification Search
CPC ........... A61B 5/00; A61B 5/05; A61B 5/0002; A61B 5/0004; A61B 5/145;
(Continued)

(56) References Cited

U.S. PATENT DOCUMENTS 3,958,560 A 5/1976 March
4,014,321 A 3/1977 March
(Continued)

FOREIGN PATENT DOCUMENTS

EP 0369942 5/1990
EP 0686372 12/1995
(Continued)

OTHER PUBLICATIONS

Su et al., "A 1.6pJ/bit 96% Stable Chip-ID Generating Circuit using Process Variations", IEEE International Solid-State Circuits Conference Digest of Technical Papers, Session 22 / Digital Circuit Innovations / 22.5, Jan. 2007, pp. 406-407, 611.
(Continued)

*Primary Examiner* — Brian Wilson
(74) *Attorney, Agent, or Firm* — Kilpatrick Townsend & Stockton LLP

(57) ABSTRACT

An eye-mountable device includes a controller embedded in a polymeric material configured for mounting to a surface of an eye. The controller is electrically connected to an antenna included in the eye-mountable device. The controller is configured to: (i) receive an indication of an interrogation signal via the antenna, (ii) responsive to the interrogation signal, output a substantially unique identification sequence; and (iii) use the antenna to communicate the substantially unique identification sequence. The substantially unique identification sequence can then be used by external readers to associate the eye-mountable device with device-specific information without storing such information on the eye-mountable device.

22 Claims, 11 Drawing Sheets

(51) Int. Cl.
*A61B 5/145* (2006.01)
*A61B 5/1477* (2006.01)
*G02C 7/04* (2006.01)

(52) U.S. Cl.
CPC .............. *A61B 5/6821* (2013.01); *G02C 7/04* (2013.01); *A61B 2560/0219* (2013.01); *A61B 2560/0223* (2013.01); *A61B 2562/028* (2013.01); *A61B 2562/085* (2013.01)

(58) Field of Classification Search
CPC . A61B 5/14532; A61B 5/1473; A61B 5/1477; A61B 5/1486; A61B 5/6821; A61B 2560/0219; A61B 2560/0223; A61B 2562/028; A61B 2562/085; C12N 9/00; G06K 7/10; G06K 7/10198; G06K 19/0717; G06K 19/0716; G01N 27/26; G01N 33/50; G02C 7/04; G08C 17/02; G08C 2201/20; G06Q 10/0833
USPC ........... 340/870.01, 500, 540, 539.1, 539.12, 340/572.1, 572.7, 572.8, 573.1, 10.1, 340/10.4; 600/345, 365, 452, 347, 383; 606/4; 204/403.01, 403.11, 403.13; 205/792
See application file for complete search history.

(56) References Cited

U.S. PATENT DOCUMENTS

| | | |
|---|---|---|
| 4,055,378 A | 10/1977 | Feneberg et al. |
| 4,122,942 A | 10/1978 | Wolfson |
| 4,136,250 A | 1/1979 | Mueller et al. |
| 4,143,949 A | 3/1979 | Chen |
| 4,153,641 A | 5/1979 | Deichert et al. |
| 4,214,014 A | 7/1980 | Hofer et al. |
| 4,309,085 A | 1/1982 | Morrison |
| 4,312,575 A | 1/1982 | Peyman et al. |
| 4,401,371 A | 8/1983 | Neefe |
| 4,463,149 A | 7/1984 | Ellis |
| 4,555,372 A | 11/1985 | Kunzler et al. |
| 4,604,479 A | 8/1986 | Ellis |
| 4,632,844 A | 12/1986 | Yanagihara et al. |
| 4,686,267 A | 8/1987 | Ellis et al. |
| 4,740,533 A | 4/1988 | Su et al. |
| 4,826,936 A | 5/1989 | Ellis |
| 4,996,275 A | 2/1991 | Ellis et al. |
| 4,997,770 A | 3/1991 | Giles et al. |
| 5,032,658 A | 7/1991 | Baron et al. |
| 5,034,461 A | 7/1991 | Lai et al. |
| 5,070,215 A | 12/1991 | Bambury et al. |
| 5,135,297 A | 8/1992 | Valint et al. |
| 5,177,165 A | 1/1993 | Valint et al. |
| 5,177,168 A | 1/1993 | Baron et al. |
| 5,219,965 A | 6/1993 | Valint et al. |
| 5,260,000 A | 11/1993 | Nandu et al. |
| 5,271,875 A | 12/1993 | Appleton et al. |
| 5,310,779 A | 5/1994 | Lai |
| 5,321,108 A | 6/1994 | Kunzler et al. |
| 5,326,584 A | 7/1994 | Kamel et al. |
| 5,336,797 A | 8/1994 | McGee et al. |
| 5,346,976 A | 9/1994 | Ellis et al. |
| 5,358,995 A | 10/1994 | Lai et al. |
| 5,364,918 A | 11/1994 | Valint, Jr. et al. |
| 5,387,662 A | 2/1995 | Kunzler et al. |
| 5,449,729 A | 9/1995 | Lai |
| 5,472,436 A | 12/1995 | Fremstad |
| 5,512,205 A | 4/1996 | Lai |
| 5,585,871 A | 12/1996 | Linden |
| 5,610,252 A | 3/1997 | Bambury et al. |
| 5,616,757 A | 4/1997 | Bambury et al. |
| 5,682,210 A | 10/1997 | Weirich |
| 5,708,094 A | 1/1998 | Lai et al. |
| 5,710,302 A | 1/1998 | Kunzler et al. |
| 5,714,557 A | 2/1998 | Kunzler et al. |
| 5,726,733 A | 3/1998 | Lai et al. |
| 5,760,100 A | 6/1998 | Nicolson et al. |
| 5,908,906 A | 6/1999 | Kunzler et al. |
| 5,981,669 A | 11/1999 | Valint et al. |
| 6,087,941 A | 7/2000 | Ferraz et al. |
| 6,131,580 A | 10/2000 | Ratner et al. |
| 6,193,369 B1 | 2/2001 | Valint et al. |
| 6,200,626 B1 | 3/2001 | Grobe et al. |
| 6,213,604 B1 | 4/2001 | Valint et al. |
| 6,297,727 B1 * | 10/2001 | Nelson, Jr. ........... G06K 19/041 340/10.1 |
| 6,312,393 B1 | 11/2001 | Abreu |
| 6,348,507 B1 | 2/2002 | Heiler et al. |
| 6,366,794 B1 | 4/2002 | Moussy et al. |
| 6,423,001 B1 | 7/2002 | Abreu |
| 6,428,839 B1 | 8/2002 | Kunzler et al. |
| 6,431,705 B1 | 8/2002 | Linden |
| 6,440,571 B1 | 8/2002 | Valint et al. |
| 6,450,642 B1 | 9/2002 | Jethmalani et al. |
| 6,532,298 B1 | 3/2003 | Cambier et al. |
| 6,550,915 B1 | 4/2003 | Grobe, III |
| 6,570,386 B2 | 5/2003 | Goldstein |
| 6,579,235 B1 | 6/2003 | Abita et al. |
| 6,599,559 B1 | 7/2003 | McGee et al. |
| 6,614,408 B1 | 9/2003 | Mann |
| 6,630,243 B2 | 10/2003 | Valint, Jr. et al. |
| 6,638,563 B2 | 10/2003 | McGee et al. |
| 6,726,322 B2 | 4/2004 | Andino et al. |
| 6,735,328 B1 | 5/2004 | Helbing et al. |
| 6,779,888 B2 | 8/2004 | Marmo |
| 6,804,560 B2 | 10/2004 | Nisch et al. |
| 6,851,805 B2 | 2/2005 | Blum et al. |
| 6,885,818 B2 | 4/2005 | Goldstein |
| 6,939,299 B1 | 9/2005 | Petersen et al. |
| 6,980,842 B2 | 12/2005 | March et al. |
| 7,018,040 B2 | 3/2006 | Blum et al. |
| 7,131,945 B2 | 11/2006 | Fink et al. |
| 7,169,106 B2 | 1/2007 | Fleischman et al. |
| 7,398,119 B2 | 7/2008 | Lambert et al. |
| 7,423,801 B2 | 9/2008 | Kaufman et al. |
| 7,429,465 B2 | 9/2008 | Muller et al. |
| 7,441,892 B2 | 10/2008 | Hsu |
| 7,443,016 B2 | 10/2008 | Tsai et al. |
| 7,450,981 B2 | 11/2008 | Jeon |
| 7,639,845 B2 | 12/2009 | Utsunomiya |
| 7,654,671 B2 | 2/2010 | Glynn |
| 7,699,465 B2 | 4/2010 | Dootjes et al. |
| 7,728,949 B2 | 6/2010 | Clarke et al. |
| 7,751,896 B2 | 7/2010 | Graf et al. |
| 7,799,243 B2 | 9/2010 | Mather et al. |
| 7,809,417 B2 | 10/2010 | Abreu |
| 7,878,650 B2 | 2/2011 | Fritsch et al. |
| 7,885,698 B2 | 2/2011 | Feldman |
| 7,907,931 B2 | 3/2011 | Hartigan et al. |
| 7,926,940 B2 | 4/2011 | Blum et al. |
| 7,931,832 B2 | 4/2011 | Pugh et al. |
| 7,964,390 B2 | 6/2011 | Rozakis et al. |
| 8,080,187 B2 | 12/2011 | Tepedino, Jr. et al. |
| 8,096,654 B2 | 1/2012 | Amirparviz et al. |
| 8,118,752 B2 | 2/2012 | Hetling et al. |
| 8,142,016 B2 | 3/2012 | Legerton et al. |
| 8,224,415 B2 | 7/2012 | Budiman |
| 2002/0049374 A1 * | 4/2002 | Abreu .................. A61B 3/1241 600/405 |
| 2002/0193674 A1 | 12/2002 | Fleischman et al. |
| 2003/0179094 A1 | 9/2003 | Abreu |
| 2004/0027536 A1 | 2/2004 | Blum et al. |
| 2004/0116794 A1 | 6/2004 | Fink et al. |
| 2005/0045589 A1 | 3/2005 | Rastogi et al. |
| 2005/0052279 A1 * | 3/2005 | Bridgelall ............ G06K 7/0008 340/10.1 |
| 2005/0221276 A1 | 10/2005 | Rozakis et al. |
| 2006/0239461 A1 * | 10/2006 | Brickell ................ H04L 9/0869 380/268 |
| 2007/0016074 A1 | 1/2007 | Abreu |
| 2007/0030443 A1 | 2/2007 | Chapoy et al. |
| 2007/0052525 A1 * | 3/2007 | Quan ................... H04L 63/0853 340/10.4 |

(56) References Cited

U.S. PATENT DOCUMENTS

| | | | |
|---|---|---|---|
| 2007/0103274 A1* | 5/2007 | Berthold | G06K 19/0723 340/10.51 |
| 2007/0121065 A1 | 5/2007 | Cox et al. | |
| 2007/0188710 A1 | 8/2007 | Hetling et al. | |
| 2008/0169906 A1* | 7/2008 | Joo | A61B 5/1178 340/10.1 |
| 2008/0208335 A1 | 8/2008 | Blum et al. | |
| 2008/0218696 A1 | 9/2008 | Mir | |
| 2009/0033863 A1 | 2/2009 | Blum et al. | |
| 2009/0036761 A1 | 2/2009 | Abreu | |
| 2009/0055120 A1* | 2/2009 | Vickery | G01D 3/022 702/104 |
| 2009/0057164 A1 | 3/2009 | Minick et al. | |
| 2009/0076367 A1 | 3/2009 | Sit et al. | |
| 2009/0118604 A1 | 5/2009 | Phan et al. | |
| 2009/0189830 A1 | 7/2009 | Deering et al. | |
| 2009/0196460 A1 | 8/2009 | Jakobs et al. | |
| 2010/0001926 A1 | 1/2010 | Amirparviz et al. | |
| 2010/0013114 A1 | 1/2010 | Bowers et al. | |
| 2010/0016704 A1 | 1/2010 | Naber et al. | |
| 2010/0028559 A1 | 2/2010 | Yan et al. | |
| 2010/0072643 A1 | 3/2010 | Pugh et al. | |
| 2010/0109175 A1 | 5/2010 | Pugh et al. | |
| 2010/0110372 A1* | 5/2010 | Pugh | B29D 11/00009 351/159.75 |
| 2010/0113901 A1 | 5/2010 | Zhang et al. | |
| 2010/0133510 A1 | 6/2010 | Kim et al. | |
| 2010/0238002 A1* | 9/2010 | Ryan | G06K 19/0707 340/10.52 |
| 2010/0249548 A1 | 9/2010 | Muller | |
| 2011/0015512 A1 | 1/2011 | Pan et al. | |
| 2011/0028807 A1 | 2/2011 | Abreu | |
| 2011/0040161 A1 | 2/2011 | Abreu | |
| 2011/0055317 A1 | 3/2011 | Vonog et al. | |
| 2011/0063568 A1 | 3/2011 | Meng et al. | |
| 2011/0084834 A1* | 4/2011 | Sabeta | G06K 19/07758 340/540 |
| 2011/0116035 A1 | 5/2011 | Fritsch et al. | |
| 2011/0157541 A1 | 6/2011 | Peyman | |
| 2011/0157544 A1 | 6/2011 | Pugh et al. | |
| 2011/0184271 A1 | 7/2011 | Veciana et al. | |
| 2011/0217205 A1 | 9/2011 | Peeters | |
| 2011/0274680 A1 | 11/2011 | Mazed et al. | |
| 2011/0286064 A1 | 11/2011 | Burles et al. | |
| 2011/0298794 A1 | 12/2011 | Freedman | |
| 2012/0026458 A1 | 2/2012 | Qiu et al. | |
| 2012/0038881 A1 | 2/2012 | Amirparviz et al. | |
| 2012/0041287 A1 | 2/2012 | Goodall et al. | |
| 2012/0041552 A1 | 2/2012 | Chuck et al. | |
| 2012/0069254 A1 | 3/2012 | Burton | |
| 2012/0075168 A1 | 3/2012 | Osterhout et al. | |
| 2012/0075574 A1 | 3/2012 | Pugh et al. | |
| 2012/0078071 A1 | 3/2012 | Bohm et al. | |
| 2012/0088258 A1 | 4/2012 | Bishop et al. | |
| 2012/0092612 A1 | 4/2012 | Binder et al. | |
| 2012/0109296 A1 | 5/2012 | Fan | |
| 2012/0177576 A1 | 7/2012 | Hu | |
| 2012/0201755 A1 | 8/2012 | Rozakis et al. | |
| 2012/0226133 A1 | 9/2012 | Wong et al. | |
| 2012/0238857 A1 | 9/2012 | Wong et al. | |
| 2012/0245444 A1 | 9/2012 | Otis et al. | |
| 2012/0259188 A1 | 10/2012 | Besling | |
| 2012/0302861 A1 | 11/2012 | Marshall et al. | |
| 2013/0090534 A1 | 4/2013 | Burns et al. | |
| 2014/0343387 A1* | 11/2014 | Pugh | A61B 5/6821 600/365 |

FOREIGN PATENT DOCUMENTS

| | | |
|---|---|---|
| EP | 1061874 | 12/2000 |
| EP | 1818008 | 8/2007 |
| EP | 1947501 | 7/2008 |
| EP | 1617757 | 8/2009 |
| EP | 2457122 | 5/2012 |
| JP | 2003195230 | 7/2003 |
| JP | 2005192938 | 7/2005 |
| JP | 2008229269 | 10/2008 |
| WO | 95/04609 | 2/1995 |
| WO | 01/16641 | 3/2001 |
| WO | 01/34312 | 5/2001 |
| WO | 03/065876 | 8/2003 |
| WO | 03102632 A2 | 12/2003 |
| WO | 2004/060431 | 7/2004 |
| WO | 2004/064629 | 8/2004 |
| WO | 2006/015315 | 2/2006 |
| WO | 2009/094643 | 7/2009 |
| WO | 2010/105728 | 9/2010 |
| WO | 2010/133317 | 11/2010 |
| WO | 2011/011344 | 1/2011 |
| WO | 2011/034592 | 3/2011 |
| WO | 2011/035228 | 3/2011 |
| WO | 2011/035262 | 3/2011 |
| WO | 2011/083105 | 7/2011 |
| WO | 2011/163080 | 12/2011 |
| WO | 2012/035429 | 3/2012 |
| WO | 2012/037455 | 3/2012 |
| WO | 2012/051167 | 4/2012 |
| WO | 2012/051223 | 4/2012 |
| WO | 2012052765 | 4/2012 |
| WO | 2012137067 A2 | 10/2012 |
| WO | 2012167597 A1 | 12/2012 |

OTHER PUBLICATIONS

Su et al., "A Digital 1.6 pJ/bit Chip Identification Circuit Using Process Variations", IEEE Journal of Solid-State Circuits, vol. 43, No. 1, Jan. 2008, pp. 69-77.

International Search Report and Written Opinion of International Application No. PCT/US2014/035086 dated Aug. 27, 2014 (mailed Aug. 28, 2014).

Bionic contact lens 'To project emails before eyes,' http://www.kurzweilai.netforums/topic/bionic-contact-lens-to-project -emails-before-eyes, Last accessed Mar. 14, 2012, 2 pages..

Brahim, et al., "Polypyrrole-hydrogel composites for the construction of clinically important biosensors," 2002, Biosensors & Bioelectronics, pp. 53-59, vol. 17.

Chen, et al., "Microfabricated Implantable Parylene-Based Wireless Passive Intraocular Pressure Sensors," Journal of Microelectromechanical Systems, Dec. 2008, pp. 1342-1351, vol. 17, No. 6.

Chu, et al., "Soft Contact-lens Sensor for Monitoring Tear Sugar as Novel Wearable Device of Body Sensor Network," http://www.ksi edu/seke/dms11/DMS/2_Kohji_Mitsubayashi.pdf, Last accessed Jul. 27, 2012, 4 pages.

"Contact Lenses: Look Into My Eyes," The Economist, Jun. 2, 2011 , http://www.econonnist.com/node/18750624/print, Last accessed Mar. 13, 2012, 8 pages.

Haders, "New Controlled Release Technologies Broaden Opportunities for Ophthalmic Therapies," Drug Delivery Technology, Jul./Aug. 2009, pp. 48-53, vol. 8, No. 7.

Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012. 5 pages.

Huang, et al., "Wrinkling of Ultrathin Polymer Films," Mater. Res. Soc. Symp. Proc., 2006, 6 pages, vol. 924, Materials Research Society.

Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.

Liao, et al., "A 3-μW CMOS Glucose Sensor for Wireless Contact-Lens Tear Glucose Monitoring ," IEEE Journal of Solid-State Circuits, Jan. 2012, pp. 335-344, vol. 47, No. 1.

Liao, et al., "A 3-μW Wirelessly Powered Cmos Glucose Sensor for an Active Contact Lens," 2011 IEEE International Solid-State Circuits Conference, Session 2, Feb. 21, 2011, 3 pages.

(56) References Cited

OTHER PUBLICATIONS

Lingley, et al., "A Single-Pixel Wireless Contact Lens Display," Journal of Micromechanics and Microengineering, 2011, pp. 1-8.
Lingley, et al., "Multipurpose integrated active contact lenses," SPIE, 2009, 2 pages.
Liu, et al., "Miniature Amperometric Self-Powered Continuous Glucose Sensor with Linear Response," Analytical Chemistry, 2012, 7 pages.
Loncar, et al., "Design and Fabrication of Silicon Photonic Crystal Optical Waveguides," Journal of Lightwave Technology, Oct. 2000, pp. 1402-1411, vol. 18, No. 10.
Murdan, "Electro-responsive drug delivery from hydrogels," Journal of Controlled Release, 2003, pp. 1-17, vol. 92.
Pandey, et al., "A Fully Integrated RF-Powered Contact Lens With a Single Element Display," IEEE Transactions On Biomedical Circuits and Systems, Dec. 2010, pp. 454-461, vol. 4, No. 6.
Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.
Selner, et al., "Novel Contact Lens Electrode Array for Multi-electrode Electroretinography (meERG)," IEEE, 2011, 2 pages.
Singh, et al., "Novel Approaches in Formulation and Drug Delivery using Contact Lenses," Journal of Basic and Clinical Pharmacy, May 2011, pp. 87-101, vol. 2, Issue 2.
Thomas, et al., "Functional Contact Lenses for Remote Health Monitoring in Developing Countries," IEEE Global Humanitarian Technology Conference, 2011, pp. 212-217, IEEE Computer Society.
Tweedie, et al., "Contact creep compliance of viscoelastic materials via nanoindentation," J. Mater. Res., Jun. 2006, pp. 1576-1589, vol. 21, No. 2, Materials Research Society.
Wall, K., "Active contact lens that lets you see like the Terminator patented," Feb. 10, 2012, http://vvww.patexia.com/feed/active-contact-lens-that-lets-you-see-like-the-terminator-patented-2407, Last accessed Mar. 28, 2012, 5 pages.
Zarbin, et al., "Nanotechnology in ophthalmology," Can J Ophthalmol, 2010, pp. 457-476, vol. 45, No. 5.
Badugu et al., "A Glucose Sensing Contact Lens: A Non-Invasive Technique for Continuous Physiological Glucose Monitoring," Journal of Fluorescence, Sep. 2003, pp. 371-374, vol. 13, No. 5.
Carlson et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu et al., "Biomedical soft contact-lens sensor for in situ ocular biomonitoring of tear contents," Biomed Microdevices, 2011, pp. 603-611, vol. 13.
Chu et al., "Soft contact lens biosensor for in situ monitoring of tear glucose as non-invasive blood sugar assessment," Talanta, 2011, pp. 960-965, vol. 83.
Ho et al., "Contact Lens With Integrated Inorganic Semiconductor Devices," Mems 2008. IEEE 21st International Conference on. IEEE, 2008., pp. 403-406.
Lahdesmaki et al., "Possibilities for Continuous Glucose Monitoring by a Functional Contact Lens," IEEE Instrumentation & Measurement Magazine, Jun. 2010, pp. 14-17.
Lingley et al., "A contact lens with integrated micro solar cells," Microsyst Technol, 2012, pp. 453-458, vol. 18.
Parviz, Babak A., "For Your Eyes Only," IEEE Spectrum, Sep. 2009, pp. 36-41.
Saeedi, E. et al., "Self-assembled crystalline semiconductor optoelectronics on glass and plastic," J. Micromech. Microeng., 2008, pp. 1-7, vol. 18.
Saeedi et al., "Self-Assembled Inorganic Micro-Display on Plastic," Micro Electro Mechanical Systems, 2007. MEMS. IEEE 20th International Conference on. IEEE, 2007., pp. 755-758.
Sensimed Triggerfish, Sensimed Brochure, 2010, 10 pages.
Shih, Yi-Chun et al., "An Inductorless DC-DC Converter for Energy Harvesting With a 1.2-μW Bandgap-Referenced Output Controller," IEEE Transactions on Circuits and Systems-Ii: Express Briefs, Dec. 2011, pp. 832-836, vol. 58, No. 12.
Shum et al., "Functional modular contact lens," Proc. of Spie, 2009, pp. 73970K-1 to 73970K-8, vol. 7397.
Stauth et al., "Self-assembled single-crystal silicon circuits on plastic," PNAS, Sep. 19, 2006, pp. 13922-13927, vol. 103, No. 38.
Yao, H. et al., "A contact lens with integrated telecommunication circuit and sensors for wireless and continuous tear glucose monitoring," J. Micromech. Microeng., 2012, pp. 1-10, vol. 22.
Yao, H. et al., "A Dual Microscal Glucose Sensor on a Contact Lens, Tested in Conditions Mimicking the Eye," Micro Electro Mechanical Systems (MEMS), 2011 IEEE 24th International Conference on. IEEE, 2011, pp. 25-28.
Yao et al., "A contact lens with embedded sensor for monitoring tear glucose level," Biosensors and Bioelectronics, 2011, pp. 3290-3296, vol. 26.
Yao, H. et al., "A Soft Hydrogel Contact Lens with an Encapsulated Sensor for Tear Glucose Monitoring," Micro Electro Mechanical Systems (MEMS), 2012 IEEE 25th International Conference on IEEE, 2012, pp. 769-772.
Yeager et al., "A 9 μA, Addressable Gent Sensor Tag for Biosignal Acquistion," IEEE Journal of Solid-State Circuits, Oct. 2010, pp. 2198-2209, vol. 45, No. 10.
Zhang et al., "Design for Ultra-Low Power Biopotential Amplifiers for Biosignal Acquistion Applications," IEEE Transactions on Biomedical Circuits and Systems, 2012, pp. 344-355, vol. 6, No. 4.

* cited by examiner

DEVICE IDENTIFICATION

BACKGROUND

Unless otherwise indicated herein, the materials described in this section are not prior art to the claims in this application and are not admitted to be prior art by inclusion in this section.

An electrochemical amperometric sensor measures a concentration of an analyte by measuring a current generated through electrochemical oxidation or reduction reactions of the analyte at a working electrode of the sensor. A reduction reaction occurs when electrons are transferred from the electrode to the analyte, whereas an oxidation reaction occurs when electrons are transferred from the analyte to the electrode. The direction of the electron transfer is dependent upon the electrical potentials applied to the working electrode. A counter electrode and/or reference electrode is used to complete a circuit with the working electrode and allow the generated current to flow. When the working electrode is appropriately biased, the output current can be proportional to the reaction rate, so as to provide a measure of the concentration of the analyte surrounding the working electrode. Ideally, the output current is linearly related to the actual concentration of the analyte, and the linear relationship can therefore be characterized by a two parameter fit (e.g., slope and intercept).

In some examples, a reagent is localized proximate the working electrode to selectively react with a desired analyte. For example, glucose oxidase can be fixed near the working electrode to react with glucose and release hydrogen peroxide, which is then electrochemically detected by the working electrode to indicate the presence of glucose. Other enzymes and/or reagents can be used to detect other analytes.

SUMMARY

An eye-mountable device includes a controller embedded in a polymeric material configured for mounting to a surface of an eye. The controller is electrically connected to an antenna included in the eye-mountable device. The controller is configured to: (i) receive an indication of an interrogation signal via the antenna, (ii) responsive to the interrogation signal, output a substantially unique identification sequence; and (iii) use the antenna to communicate the substantially unique identification sequence. The substantially unique identification sequence can then be used to associate the eye-mountable device with device-specific information without storing such information on the eye-mountable device. As such, the eye-mountable device can be associated with device-specific information while being free of programmable memory.

Some embodiments of the present disclosure provide an eye-mountable device including a transparent polymeric material, a substrate, an antenna, and a controller. The transparent polymeric material can have a concave surface and a convex surface. The concave surface can be configured to be removably mounted over a corneal surface and the convex surface can be configured to be compatible with eyelid motion when the concave surface is so mounted. The substrate cab be at least partially embedded within the transparent polymeric material. The antenna can be disposed on the substrate. The controller can be electrically connected to the antenna and can be configured to: (i) receive an indication of an interrogation signal via the antenna, (ii) responsive to the interrogation signal, output a substantially unique identification sequence; and (iii) use the antenna to communicate the substantially unique identification sequence.

Some embodiments of the present disclosure provide a method. The method can include transmitting an interrogation signal to an eye-mountable device. The method can include receiving, from the eye-mountable device, a response signal indicative of a substantially unique identification sequence. The method can include associating the eye-mountable device with device-specific information based on the substantially unique identification sequence.

Some embodiments of the present disclosure provide a non-transitory computer readable medium storing instructions that, when executed by one or more processors in a computing device, cause the computing device to perform operations. The operations can include transmitting an interrogation signal to an eye-mountable device. The operations can include receiving, from the eye-mountable device, a response signal indicative of a substantially unique identification sequence. The operations can include associating the eye-mountable device with device-specific information based on the substantially unique identification sequence.

Some embodiments of the present disclosure provide a body-mountable device including a bio-compatible polymeric material, a substrate, an antenna, and a controller. The substrate can be at least partially embedded within the bio-compatible polymeric material. The antenna can be disposed on the substrate. The controller can be electrically connected to the antenna and configured to: (i) receive an indication of an interrogation signal via the antenna, (ii) responsive to the interrogation signal, output a substantially unique identification sequence; and (iii) use the antenna to communicate the substantially unique identification sequence.

Some embodiments include means for transmitting an interrogation signal to an eye-mountable device. Some embodiments include means for receiving, from the eye-mountable device, a response signal indicative of a substantially unique identification sequence. Some embodiments include means for associating the eye-mountable device with device-specific information based on the substantially unique identification sequence.

Some embodiments include means for associating an eye-mountable device with device-specific information without storing information in programmable memory included in the eye-mountable device. Some embodiments include means for implementing an eye-mountable device without including programmable memory.

These as well as other aspects, advantages, and alternatives, will become apparent to those of ordinary skill in the art by reading the following detailed description, with reference where appropriate to the accompanying figures.

DETAILED DESCRIPTION

Figure 1:
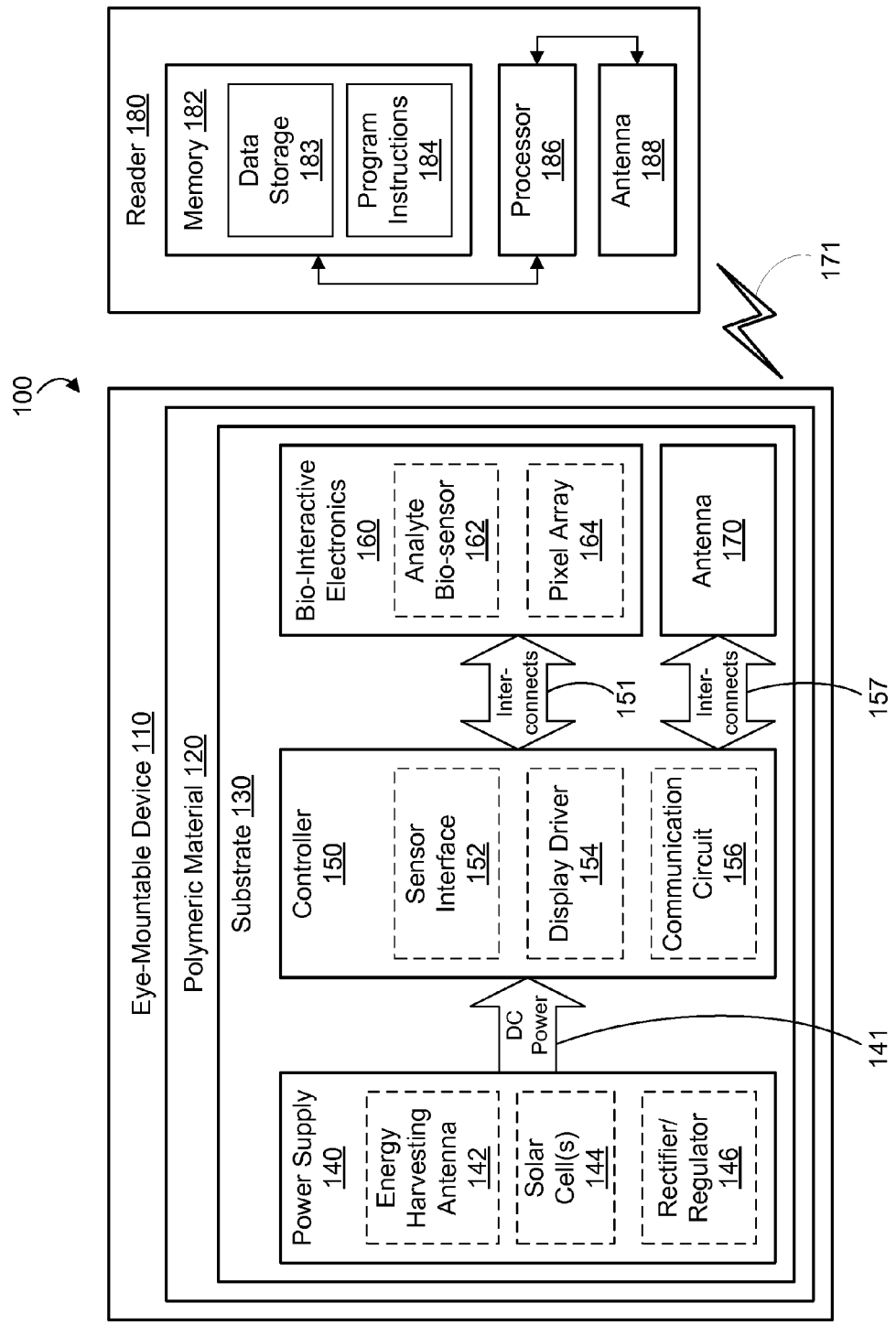
FIG. 1 is a block diagram of an example system that includes an eye-mountable device in wireless communication with an external reader.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

An ophthalmic sensing platform or implantable sensing platform can include a sensor, control electronics and an antenna all situated on a substrate embedded in a polymeric material. The polymeric material can be incorporated in an ophthalmic device, such as an eye-mountable device or an implantable medical device. The control electronics can operate the sensor to perform readings and can operate the antenna to wirelessly communicate the readings from the sensor to an external reader via the antenna. The sensing platform can be configured to output a substantially unique identification sequence and communicate the sequence to the reader. The reader can then identify a particular device based on the identification sequence, and associate device-specific information with the particular device. As such, any device-specific information, such as configuration/calibration data and the like can be stored in the reader (or a database in accessible by the reader), and the sensing platform can be implemented without any programmable memory.

The polymeric material can be in the form of a round lens with a concave curvature configured to mount to a corneal surface of an eye. An opposing convex surface can be configured to avoid interference with eyelid motion while the eye-mountable device is mounted to the eye. The substrate, and electronics components mounted thereon, can be embedded near the periphery of the polymeric material to avoid interference with incident light received closer to the central region of the cornea. The eye-mountable device can be powered via harvested energy received by the eye-mountable device. For example, the device can be powered by photovoltaic cells included on the sensing platform that are energized by incident light. Additionally or alternatively, power can be provided by radio frequency energy inductively harvested using the antenna. For example, power can be provided by rectifying voltage variations on the leads of the antenna from energy received via an electromagnetic coupling. A rectifier and/or regulator can be incorporated with the control electronics to generate a stable DC voltage to power the remaining electronics components. The antenna can be arranged as a loop of conductive material with leads connected to the control electronics. In some embodiments, such a loop antenna can also wirelessly communicate with an external reader by modifying the impedance of the loop antenna so as to characteristically modify backscatter radiation from the antenna. In some embodiments, the loop antenna, or a second antenna either on the substrate or included in the control chip, may actively broadcast a signal to be received by an external reader. Such active broadcast may be in addition to, or as an alternative to, modulated backscatter radiation from an energy-harvesting antenna.

Tear fluid contains a variety of inorganic electrolytes (e.g., $Ca^{2+}$, $Mg^{2+}$, $Cl^-$), organic components (e.g., glucose, lactate, proteins, lipids, etc.), and so on that can be used to diagnose health states. The eye-mountable device may include an electrochemical amperometric sensor or another bio-sensor configured to measure concentrations of one or more analytes. An eye-mountable device configured to measure one or more of these analytes can thus provide a convenient non-invasive platform useful in diagnosing and/or monitoring health states. For example, an eye-mountable device can be configured to sense glucose and can be used by diabetic individuals to measure/monitor their glucose levels.

The eye-mountable device, and associated reader, can operate to repeatedly obtain measurements and communicate the results back to the reader. The eye-mountable device can obtain measurements and transmit responsive signals to the reader whenever it receives sufficient radio frequency radiation to power the sensor platform to turn on via inductively harvested energy.

The eye-mountable device can be implemented without on-board programmable memory. Instead, device-specific information such as calibration information (or other configuration information), historical sensor readings (or other user-specific information) can be stored in the external reader or in a database accessible to the reader. Device-specific information may also include, for example, thresholds for alerts related to sensor data readings, user preferences, configuration settings. For example, the device-specific information may specify the sampling frequency for a biosensor included in the eye-mountable device (or other conditions of the operation of the biosensor). To associate such device-specific information with a particular eye-mountable device, the eye-mountable device can be configured to generate and output a distinctive signature, such as a substantially unique identification sequence. The identification sequence can be communicated to the reader, which can then associate a particular eye-mountable device with corresponding device-specific information using the substantially unique identification sequence to distinguish between different eye-mountable devices. The substantially unique identification sequence can be a data series that can be repeatedly (i.e., consistently) generated by the eye-mountable device in response to an interrogation signal. In some cases, the data series is hard-coded into the control electronics of the eye-mountable device (e.g., during device manufacture) akin to a serial number. In some cases, the data series is generated dynamically (but repeatably) in accordance with process variations in a series of circuit components. For instance, a series of binary bits can be constructed from the output of a set of comparator circuits that each settle in one state or another depending on the difference in threshold voltage between two TFTs.

For eye-mountable devices equipped with electrochemical bio-sensors, device-specific information can include sensor calibration information. The calibration information may related to interpreting results (e.g., current offsets, current/voltage slope information, etc.). Such calibration information can then be used by the reader in interpreting the sensor readings as indications of analyte levels (e.g., mapping sensor readings to analyte concentrations). The calibration information may be based on a manufacturing batch of a particular eye-mountable device. Additionally or alternatively, calibration information may be based on previously obtained calibration results for a particular eye-mountable device. The device-specific information may additionally or alternatively include sensor configuration information and/or user preferences for operating the sensor (e.g., voltage offset settings, sensor stabilization durations, measurement frequencies, etc.). Such configuration information can then be used to cause the eye-mountable device to obtain measurements in accordance with the configuration information. For example, an indication of sensor stabilization time can cause the reader to initiate a stabilization operation prior to obtaining a sensor measurement with a duration specified in the configuration information.

Configuring the eye-mountable device without programmable memory, and instead storing device-specific information in the external reader or in a database accessible to the external reader, allows the eye-mountable device to operate at a reduced power budget. Historical sensor readings for a particular user can also be loaded to an external reader or database to allow the user to track their readings over time, without relying on the resiliency/longevity of any one particular eye-mountable device, which may be disposable. In addition, such eye-mountable devices can be disposed without losing any user-specific or user-sensitive information (e.g., bio-sensor measurements), because such information is stored only on the external reader and/or networked database.

II. Example Ophthalmic Electronics Platform

FIG. 1 is a block diagram of a system 100 that includes an eye-mountable device 110 in wireless communication with an external reader 180. The exposed regions of the eye-mountable device 110 are made of a polymeric material 120 formed to be contact-mounted to a corneal surface of an eye. A substrate 130 is embedded in the polymeric material 120 to provide a mounting surface for a power supply 140, a controller 150, bio-interactive electronics 160, and a communication antenna 170. The bio-interactive electronics 160 are operated by the controller 150. The power supply 140 supplies operating voltages to the controller 150 and/or the bio-interactive electronics 160. The antenna 170 is operated by the controller 150 to communicate information to and/or from the eye-mountable device 110. The antenna 170, the controller 150, the power supply 140, and the bio-interactive electronics 160 can all be situated on the embedded substrate 130. Because the eye-mountable device 110 includes electronics and is configured to be contact-mounted to an eye, it is also referred to herein as an ophthalmic electronics platform.

To facilitate contact-mounting, the polymeric material 120 can have a concave surface configured to adhere ("mount") to a moistened corneal surface (e.g., by capillary forces with a tear film coating the corneal surface). Additionally or alternatively, the eye-mountable device 110 can be adhered by a vacuum force between the corneal surface and the polymeric material due to the concave curvature. While mounted with the concave surface against the eye, the outward-facing surface of the polymeric material 120 can have a convex curvature that is formed to not interfere with eye-lid motion while the eye-mountable device 110 is mounted to the eye. For example, the polymeric material 120 can be a substantially transparent curved polymeric disk shaped similarly to a contact lens.

The polymeric material 120 can include one or more biocompatible materials, such as those employed for use in contact lenses or other ophthalmic applications involving direct contact with the corneal surface. The polymeric material 120 can optionally be formed in part from such biocompatible materials or can include an outer coating with such biocompatible materials. The polymeric material 120 can include materials configured to moisturize the corneal surface, such as hydrogels and the like. In some embodiments, the polymeric material 120 can be a deformable ("non-rigid") material to enhance wearer comfort. In some embodiments, the polymeric material 120 can be shaped to provide a predetermined, vision-correcting optical power, such as can be provided by a contact lens.

The substrate 130 includes one or more surfaces suitable for mounting the bio-interactive electronics 160, the controller 150, the power supply 140, and the antenna 170. The substrate 130 can be employed both as a mounting platform for chip-based circuitry (e.g., by flip-chip mounting to connection pads) and/or as a platform for patterning conductive materials (e.g., gold, platinum, palladium, titanium, copper, aluminum, silver, metals, other conductive materials, combinations of these, etc.) to create electrodes, interconnects, connection pads, antennae, etc. In some embodiments, substantially transparent conductive materials (e.g., indium tin oxide) can be patterned on the substrate 130 to form circuitry, electrodes, etc. For example, the antenna 170 can be formed by forming a pattern of gold or another conductive material on the substrate 130 by deposition, photolithography, electroplating, etc. Similarly, interconnects 151, 157 between the controller 150 and the bio-interactive electronics 160, and between the controller 150 and the antenna 170, respectively, can be formed by depositing suitable patterns of conductive materials on the substrate 130. A combination of microfabrication techniques including, without limitation, the use of photoresists, masks, deposition techniques, and/or plating techniques can be employed to pattern materials on the substrate 130. The substrate 130 can be a relatively rigid material, such as polyethylene terephthalate ("PET") or another material configured to structurally support the circuitry and/or chip-based electronics within the polymeric material 120. The eye-mountable device 110 can alternatively be arranged with a group of unconnected substrates rather than a single substrate. For example, the controller 150 and a bio-sensor or other bio-interactive electronic component can be mounted to one substrate, while the antenna 170 is mounted to another substrate and the two can be electrically connected via the interconnects 157.

In some embodiments, the bio-interactive electronics 160 (and the substrate 130) can be positioned away from the center of the eye-mountable device 110 and thereby avoid interference with light transmission to the central, light-sensitive region of the eye. For example, where the eye-mountable device 110 is shaped as a concave-curved disk, the substrate 130 can be embedded around the periphery (e.g., near the outer circumference) of the disk. In some embodiments, however, the bio-interactive electronics 160 (and the substrate 130) can be positioned in or near the central region of the eye-mountable device 110. Additionally or alternatively, the bio-interactive electronics 160 and/or substrate 130 can be substantially transparent to incoming visible light to mitigate interference with light transmission to the eye. Moreover, in some embodiments, the bio-interactive electronics 160 can include a pixel array 164 that emits and/or transmits light to be received by the eye according to display instructions. Thus, the bio-interactive electronics 160 can optionally be positioned in the center of the eye-mountable device so as to generate perceivable visual cues to a wearer of the eye-mountable device 110, such as by displaying information (e.g., characters, symbols, flashing patterns, etc.) on the pixel array 164.

The substrate 130 can be shaped as a flattened ring with a radial width dimension sufficient to provide a mounting platform for the embedded electronics components. The substrate 130 can have a thickness sufficiently small to allow the substrate 130 to be embedded in the polymeric material 120 without influencing the profile of the eye-mountable device 110. The substrate 130 can have a thickness sufficiently large to provide structural stability suitable for supporting the electronics mounted thereon. For example, the substrate 130 can be shaped as a ring with a diameter of about 10 millimeters, a radial width of about 1 millimeter (e.g., an outer radius 1 millimeter larger than an inner radius), and a thickness of about 50 micrometers. The substrate 130 can optionally be aligned with the curvature of the eye-mounting surface of the eye-mountable device 110 (e.g., convex surface). For example, the substrate 130 can be shaped along the surface of an imaginary cone between two circular segments that define an inner radius and an outer radius. In such an example, the surface of the substrate 130 along the surface of the imaginary cone defines an inclined surface that is approximately aligned with the curvature of the eye mounting surface at that radius.

The power supply 140 is configured to harvest ambient energy to power the controller 150 and bio-interactive electronics 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the external reader 180. That is, the functions of the communication antenna 170 and the energy harvesting antenna 142 can be accomplished with the same physical antenna.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the bio-interactive electronics 160 and the antenna 170. The controller 150 can include logic circuitry configured to operate the bio-interactive electronics 160 so as to interact with a biological environment of the eye-mountable device 110. The interaction could involve the use of one or more components, such an analyte bio-sensor 162, in bio-interactive electronics 160 to obtain input from the biological environment. Additionally or alternatively, the interaction could involve the use of one or more components, such as pixel array 164, to provide an output to the biological environment.

In one example, the controller 150 includes a sensor interface module 152 that is configured to operate analyte bio-sensor 162. The analyte bio-sensor 162 can be, for example, an amperometric electrochemical sensor that includes a working electrode and a reference electrode. A voltage can be applied between the working and reference electrodes to cause an analyte to undergo an electrochemical reaction (e.g., a reduction and/or oxidation reaction) at the working electrode. The electrochemical reaction can generate an amperometric current that can be measured through the working electrode. The amperometric current can be dependent on the analyte concentration. Thus, the amount of the amperometric current that is measured through the working electrode can provide an indication of analyte concentration. In some embodiments, the sensor interface module 152 can be a potentiostat configured to apply a voltage difference between working and reference electrodes while measuring a current through the working electrode.

In some instances, a reagent can also be included to sensitize the electrochemical sensor to one or more desired analytes. For example, a layer of glucose oxidase ("GOx") proximal to the working electrode can catalyze glucose oxidation to generate hydrogen peroxide ($H_2O_2$). The hydrogen peroxide can then be electro-oxidized at the working electrode, which releases electrons to the working electrode, resulting in an amperometric current that can be measured through the working electrode.

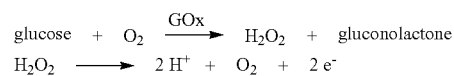

The current generated by either reduction or oxidation reactions is approximately proportionate to the reaction rate. Further, the reaction rate is dependent on the rate of analyte molecules reaching the electrochemical sensor electrodes to fuel the reduction or oxidation reactions, either directly or catalytically through a reagent. In a steady state, where analyte molecules diffuse to the electrochemical sensor electrodes from a sampled region at approximately the same rate that additional analyte molecules diffuse to the sampled region from surrounding regions, the reaction rate is approximately proportionate to the concentration of the analyte molecules. The current measured through the working electrode thus provides an indication of the analyte concentration.

The controller 150 can optionally include a display driver module 154 for operating a pixel array 164. The pixel array 164 can be an array of separately programmable light transmitting, light reflecting, and/or light emitting pixels arranged in rows and columns. The individual pixel circuits can optionally include liquid crystal technologies, microelectromechanical technologies, emissive diode technologies, etc. to selectively transmit, reflect, and/or emit light according to information from the display driver module 154. Such a pixel array 164 can also optionally include more than one color of pixels (e.g., red, green, and blue pixels) to render visual content in color. The display driver module 154 can include, for example, one or more data lines providing programming information to the separately programmed pixels in the pixel array 164 and one or more addressing lines for setting groups of pixels to receive such programming information. Such a pixel array 164 situated on the eye can also include one or more lenses to direct light from the pixel array to a focal plane perceivable by the eye.

The controller 150 can also include a communication circuit 156 for sending and/or receiving information via the antenna 170. The communication circuit 156 can optionally include one or more oscillators, mixers, frequency injectors, etc. to modulate and/or demodulate information on a carrier frequency to be transmitted and/or received by the antenna 170. In some examples, the eye-mountable device 110 is configured to indicate an output from a bio-sensor by modulating an impedance of the antenna 170 in a manner that is perceivable by the external reader 180. For example, the communication circuit 156 can cause variations in the amplitude, phase, and/or frequency of backscatter radiation from the antenna 170, and such variations can be detected by the reader 180.

The controller 150 is connected to the bio-interactive electronics 160 via interconnects 151. For example, where the controller 150 includes logic elements implemented in an integrated circuit to form the sensor interface module 152 and/or display driver module 154, a patterned conductive material (e.g., gold, platinum, palladium, titanium, copper, aluminum, silver, metals, combinations of these, etc.) can connect a terminal on the chip to the bio-interactive electronics 160. Similarly, the controller 150 is connected to the antenna 170 via interconnects 157.

It is noted that the block diagram shown in FIG. 1 is described in connection with functional modules for convenience in description. However, embodiments of the eye-mountable device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the eye-mountable device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna 170 can be implemented with the same physical antenna. For example, a loop antenna can both harvest incident radiation for power generation and communicate information via backscatter radiation.

The external reader 180 includes an antenna 188 (or a group of more than one antennae) to send and receive wireless signals 171 to and from the eye-mountable device 110. The external reader 180 also includes a computing system with a processor 186 in communication with a memory 182. The memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the eye-mountable device 110 and/or external reader 180), etc. The memory 182 can also include program instructions 184 for execution by the processor 186 to cause the external reader 180 to perform processes specified by the instructions 184. For example, the program instructions 184 can cause external reader 180 to provide a user interface that allows for retrieving information communicated from the eye-mountable device 110 (e.g., sensor outputs from the analyte bio-sensor 162). The external reader 180 can also include one or more hardware components for operating the antenna 188 to send and receive the wireless signals 171 to and from the eye-mountable device 110. For example, oscillators, frequency injectors, encoders, decoders, amplifiers, filters, etc. can drive the antenna 188 according to instructions from the processor 186.

The external reader 180 can be a smart phone, digital assistant, or other portable computing device with wireless connectivity sufficient to provide the wireless communication link 171. The external reader 180 can also be implemented as an antenna module that can be plugged in to a portable computing device, such as in an example where the communication link 171 operates at carrier frequencies not commonly employed in portable computing devices. In some instances, the external reader 180 is a special-purpose device configured to be worn relatively near a wearer's eye to allow the wireless communication link 171 to operate with a low power budget. For example, the external reader 180 can be integrated in a piece of jewelry such as a necklace, earing, etc. or integrated in an article of clothing worn near the head, such as a hat, headband, etc.

In an example where the eye-mountable device 110 includes an analyte bio-sensor 162, the system 100 can be operated to monitor the analyte concentration in tear film on the surface of the eye. Thus, the eye-mountable device 110 can be configured as a platform for an ophthalmic analyte bio-sensor. The tear film is an aqueous layer secreted from the lacrimal gland to coat the eye. The tear film is in contact with the blood supply through capillaries in the structure of the eye and includes many biomarkers found in blood that are analyzed to characterize a person's health condition(s). For example, the tear film includes glucose, calcium, sodium, cholesterol, potassium, other biomarkers, etc. The biomarker concentrations in the tear film can be systematically different than the corresponding concentrations of the biomarkers in the blood, but a relationship between the two concentration levels can be established to map tear film biomarker concentration values to blood concentration levels. For example, the tear film concentration of glucose can be established (e.g., empirically determined) to be approximately one tenth the corresponding blood glucose concentration. Although another ratio relationship and/or a non-ratio relationship may be used. Thus, measuring tear film analyte concentration levels provides a non-invasive technique for monitoring biomarker levels in comparison to blood sampling techniques performed by lancing a volume of blood to be analyzed outside a person's body. Moreover, the ophthalmic analyte bio-sensor platform disclosed here can be operated substantially continuously to enable real time monitoring of analyte concentrations.

To perform a reading with the system 100 configured as a tear film analyte monitor, the external reader 180 can emit radio frequency radiation 171 that is harvested to power the eye-mountable device 110 via the power supply 140. Radio frequency electrical signals captured by the energy harvesting antenna 142 (and/or the communication antenna 170) are rectified and/or regulated in the rectifier/regulator 146 and a regulated DC supply voltage 147 is provided to the controller 150. The radio frequency radiation 171 thus turns on the electronic components within the eye-mountable device 110. Once turned on, the controller 150 operates the analyte bio-sensor 162 to measure an analyte concentration level. For example, the sensor interface module 152 can apply a voltage between a working electrode and a reference electrode in the analyte bio-sensor 162. The applied voltage can be sufficient to cause the analyte to undergo an electrochemical reaction at the working electrode and thereby generate an amperometric current that can be measured through the working electrode. The measured amperometric current can provide the sensor reading ("result") indicative of the analyte concentration. The controller 150 can operate the antenna 170 to communicate the sensor reading back to the external reader 180 (e.g., via the communication circuit 156). The sensor reading can be communicated by, for example, modulating an impedance of the communication antenna 170 such that the modulation in impedance is detected by the external reader 180. The modulation in antenna impedance can be detected by, for example, backscatter radiation from the antenna 170.

In some embodiments, the system 100 can operate to non-continuously ("intermittently") supply energy to the eye-mountable device 110 to power the controller 150 and electronics 160. For example, radio frequency radiation 171 can be supplied to power the eye-mountable device 110 long enough to carry out a tear film analyte concentration measurement and communicate the results. For example, the supplied radio frequency radiation can provide sufficient power to apply a potential between a working electrode and a reference electrode sufficient to induce electrochemical reactions at the working electrode, measure the resulting amperometric current, and modulate the antenna impedance to adjust the backscatter radiation in a manner indicative of the measured amperometric current. In such an example, the supplied radio frequency radiation 171 can be considered an interrogation signal from the external reader 180 to the eye-mountable device 110 to request a measurement. By periodically interrogating the eye-mountable device 110 (e.g., by supplying radio frequency radiation 171 to temporarily turn the device on) and storing the sensor results (e.g., via the data storage 183), the external reader 180 can accumulate a set of analyte concentration measurements over time without continuously powering the eye-mountable device 110.

Figure 2A:
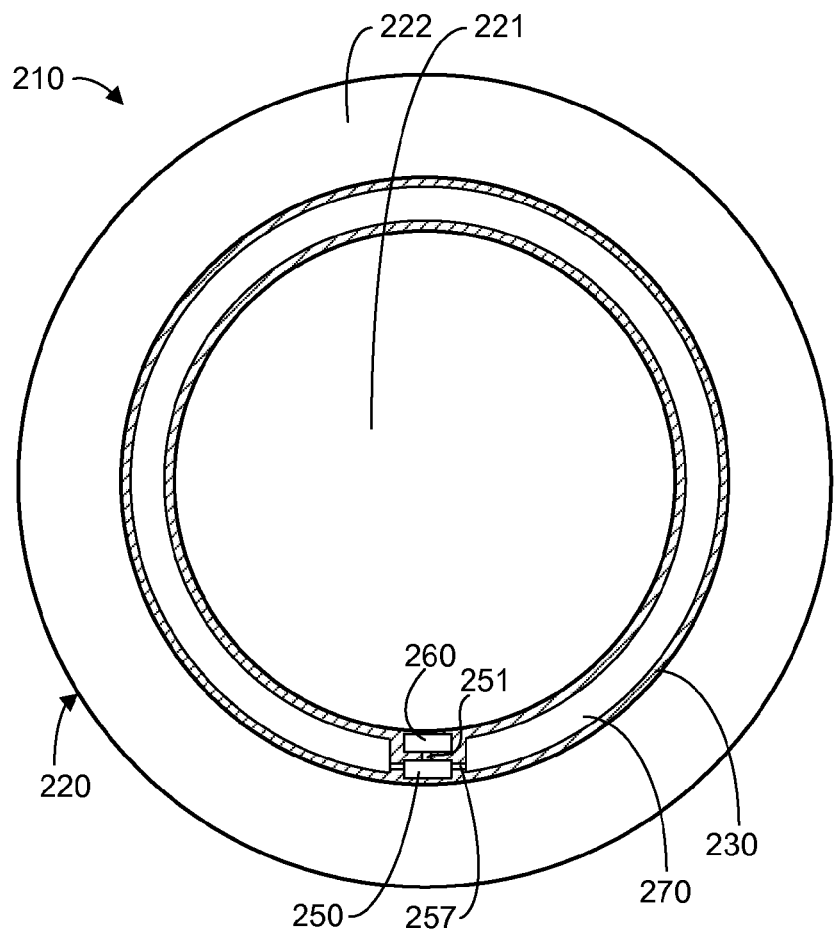
FIG. 2A is a top view of an example eye-mountable device.
Figure 2B:
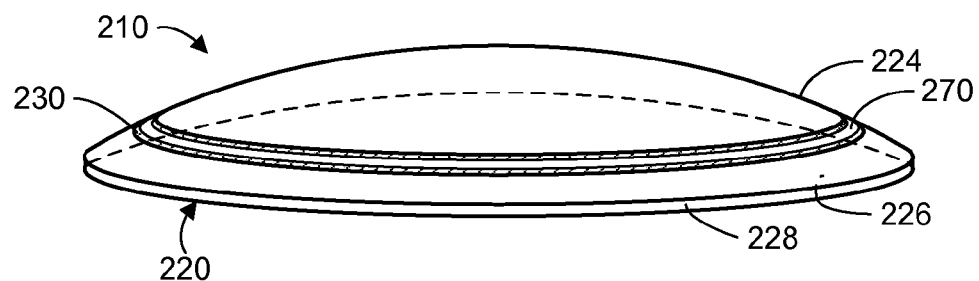
FIG. 2B is a side view of the example eye-mountable device shown in FIG. 2A.

FIG. 2A is a top view of an example eye-mountable electronic device 210 (or ophthalmic electronics platform). FIG. 2B is an aspect view of the example eye-mountable electronic device shown in FIG. 2A. It is noted that relative dimensions in FIGS. 2A and 2B are not necessarily to scale, but have been rendered for purposes of explanation only in describing the arrangement of the example eye-mountable electronic device 210. The eye-mountable device 210 is formed of a polymeric material 220 shaped as a curved disk. The polymeric material 220 can be a substantially transparent material to allow incident light to be transmitted to the eye while the eye-mountable device 210 is mounted to the eye. The polymeric material 220 can be a biocompatible material similar to those employed to form vision correction and/or cosmetic contact lenses in optometry, such as polyethylene terephthalate ("PET"), polymethyl methacrylate ("PMMA"), polyhydroxyethylmethacrylate ("poly-HEMA"), silicone hydrogels, combinations of these, etc. The polymeric material 220 can be formed with one side having a concave surface 226 suitable to fit over a corneal surface of an eye. The opposite side of the disk can have a convex surface 224 that does not interfere with eyelid motion while the eye-mountable device 210 is mounted to the eye. A circular outer side edge 228 connects the concave surface 224 and convex surface 226.

The eye-mountable device 210 can have dimensions similar to a vision correction and/or cosmetic contact lenses, such as a diameter of approximately 1 centimeter, and a thickness of about 0.1 to about 0.5 millimeters. However, the diameter and thickness values are provided for explanatory purposes only. In some embodiments, the dimensions of the eye-mountable device 210 can be selected according to the size and/or shape of the corneal surface of the wearer's eye.

The polymeric material 220 can be formed with a curved shape in a variety of ways. For example, techniques similar to those employed to form vision-correction contact lenses, such as heat molding, injection molding, spin casting, etc. can be employed to form the polymeric material 220. While the eye-mountable device 210 is mounted in an eye, the convex surface 224 faces outward to the ambient environment while the concave surface 226 faces inward, toward the corneal surface. The convex surface 224 can therefore be considered an outer, top surface of the eye-mountable device 210 whereas the concave surface 226 can be considered an inner, bottom surface. The "bottom" view shown in FIG. 2A is facing the concave surface 226. From the bottom view shown in FIG. 2A, the outer periphery 222, near the outer circumference of the curved disk is curved to extend out of the page, whereas the central region 221, near the center of the disk is curved to extend into the page.

A substrate 230 is embedded in the polymeric material 220. The substrate 230 can be embedded to be situated along the outer periphery 222 of the polymeric material 220, away from the central region 221. The substrate 230 does not interfere with vision because it is too close to the eye to be in focus and is positioned away from the central region 221 where incident light is transmitted to the eye-sensing portions of the eye. Moreover, the substrate 230 can be formed of a transparent material to further mitigate effects on visual perception.

The substrate 230 can be shaped as a flat, circular ring (e.g., a disk with a centered hole). The flat surface of the substrate 230 (e.g., along the radial width) is a platform for mounting electronics such as chips (e.g., via flip-chip mounting) and for patterning conductive materials (e.g., via microfabrication techniques such as photolithography, deposition, plating, etc.) to form electrodes, antenna(e), and/or interconnections. The substrate 230 and the polymeric material 220 can be approximately cylindrically symmetric about a common central axis. The substrate 230 can have, for example, a diameter of about 10 millimeters, a radial width of about 1 millimeter (e.g., an outer radius 1 millimeter greater than an inner radius), and a thickness of about 50 micrometers. However, these dimensions are provided for example purposes only, and in no way limit the present disclosure. The substrate 230 can be implemented in a variety of different form factors, similar to the discussion of the substrate 130 in connection with FIG. 1 above.

A loop antenna 270, controller 250, and bio-interactive electronics 260 are disposed on the embedded substrate 230. The controller 250 can be a chip including logic elements configured to operate the bio-interactive electronics 260 and the loop antenna 270. The controller 250 is electrically connected to the loop antenna 270 by interconnects 257 also situated on the substrate 230. Similarly, the controller 250 is electrically connected to the bio-interactive electronics 260 by an interconnect 251. The interconnects 251, 257, the loop antenna 270, and any conductive electrodes (e.g., for an electrochemical analyte bio-sensor, etc.) can be formed from conductive materials patterned on the substrate 230 by a process for precisely patterning such materials, such as deposition, photolithography, etc. The conductive materials patterned on the substrate 230 can be, for example, gold, platinum, palladium, titanium, carbon, aluminum, copper, silver, silver-chloride, conductors formed from noble materials, metals, combinations of these, etc.

As shown in FIG. 2A, which is a view facing the convex surface 224 of the eye-mountable device 210, the bio-interactive electronics module 260 is mounted to a side of the substrate 230 facing the convex surface 224. Where the bio-interactive electronics module 260 includes an analyte bio-sensor, for example, mounting such a bio-sensor on the substrate 230 to be close to the convex surface 224 allows the bio-sensor to sense analyte concentrations in tear film 42 coating the convex surface 224 of the polymeric material 220 (e.g., a tear film layer distributed by eyelid motion). However, the electronics, electrodes, etc. situated on the substrate 230 can be mounted to either the "inward" facing side (e.g., situated closest to the concave surface 226) or the "outward" facing side (e.g., situated closest to the convex surface 224). Moreover, in some embodiments, some electronic components can be mounted on one side of the substrate 230, while other electronic components are mounted to the opposing side, and connections between the two can be made through conductive materials passing through the substrate 230.

The loop antenna 270 is a layer of conductive material patterned along the flat surface of the substrate to form a flat conductive ring. In some instances, the loop antenna 270 can be formed without making a complete loop. For instances, the antenna 270 can have a cutout to allow room for the controller 250 and bio-interactive electronics 260, as illustrated in FIG. 2A. However, the loop antenna 270 can also be arranged as a continuous strip of conductive material that wraps entirely around the flat surface of the substrate 230 one or more times. For example, a strip of conductive material with multiple windings can be patterned on the side of the substrate 230 opposite the controller 250 and bio-interactive electronics 260. Interconnects between the ends of such a wound antenna (e.g., the antenna leads) can then be passed through the substrate 230 to the controller 250.

Figure 2D:
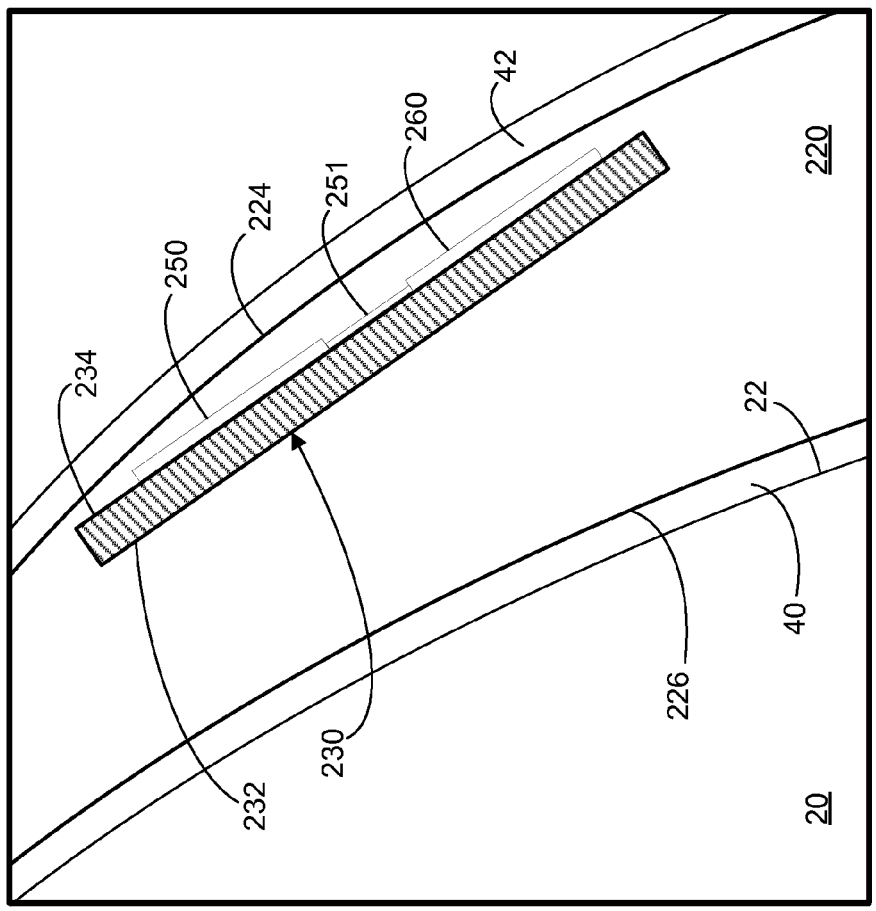
FIG. 2D is a side cross-section view enhanced to show the tear film layers surrounding the surfaces of the example eye-mountable device when mounted as shown in FIG. 2C.
Figure 2C:
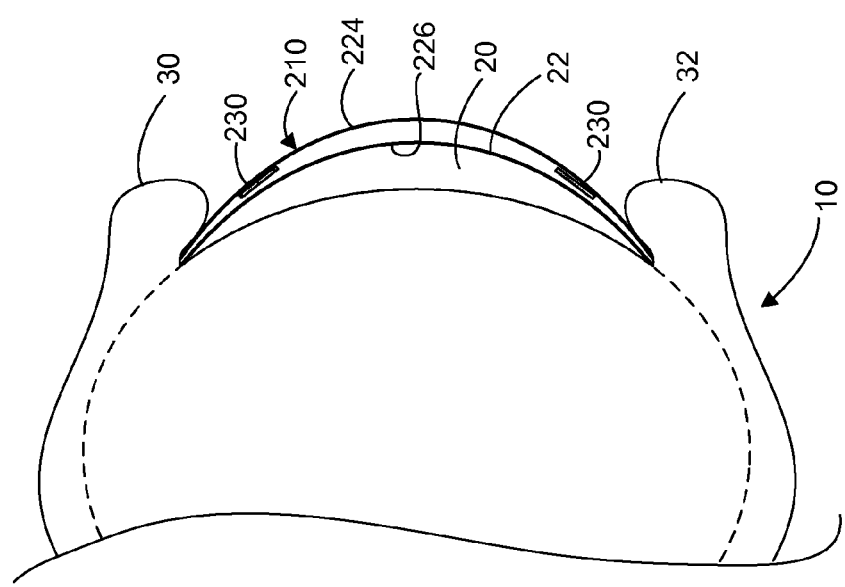
FIG. 2C is a side cross-section view of the example eye-mountable device shown in FIGS. 2A and 2B while mounted to a corneal surface of an eye.

FIG. 2C is a side cross-section view of the example eye-mountable electronic device 210 while mounted to a corneal surface 22 of an eye 10. FIG. 2D is a close-in side cross-section view enhanced to show the tear film layers 40, 42 surrounding the exposed surfaces 224, 226 of the example eye-mountable device 210. It is noted that relative dimensions in FIGS. 2C and 2D are not necessarily to scale, but have been rendered for purposes of explanation only in describing the arrangement of the example eye-mountable electronic device 210. For example, the total thickness of the eye-mountable device can be about 200 micrometers, while the thickness of the tear film layers 40, 42 can each be about 10 micrometers, although this ratio may not be reflected in the figures. Some aspects are exaggerated to allow for illustration and facilitate explanation.

The eye 10 includes a cornea 20 that is covered by bringing the upper eyelid 30 and lower eyelid 32 together over the top of the eye 10. Incident light is received by the eye 10 through the cornea 20, where light is optically directed to light sensing elements of the eye 10 (e.g., rods and cones, etc.) to stimulate visual perception. The motion of the eyelids 30, 32 distributes a tear film across the exposed corneal surface 22 of the eye 10. The tear film is an aqueous solution secreted by the lacrimal gland to protect and lubricate the eye 10. When the eye-mountable device 210 is mounted in the eye 10, the tear film coats both the concave and convex surfaces 224, 226 with an inner layer 40 (along the concave surface 226) and an outer layer 42 (along the convex layer 224). The tear film layers 40, 42 can be about 10 micrometers in thickness and together account for about 10 microliters.

The tear film layers 40, 42 are distributed across the corneal surface 22 and/or the convex surface 224 by motion of the eyelids 30, 32. For example, the eyelids 30, 32 raise and lower, respectively, to spread a small volume of tear film across the corneal surface 22 and/or the convex surface 224 of the eye-mountable device 210. The tear film layer 40 on the corneal surface 22 also facilitates mounting the eye-mountable device 210 by capillary forces between the concave surface 226 and the corneal surface 22. In some embodiments, the eye-mountable device 210 can also be held over the eye in part by vacuum forces against corneal surface 22 due to the concave curvature of the eye-facing concave surface 226.

As shown in the cross-sectional views in FIGS. 2C and 2D, the substrate 230 can be inclined such that the flat mounting surfaces of the substrate 230 are approximately parallel to the adjacent portion of the convex surface 224. As described above, the substrate 230 is a flattened ring with an inward-facing surface 232 (closer to the concave surface 226 of the polymeric material 220) and an outward-facing surface 234 (closer to the convex surface 224). The substrate 230 can have electronic components and/or patterned conductive materials mounted to either or both mounting surfaces 232, 234. As shown in FIG. 2D, the sensor electronics 260, controller 250, and conductive interconnect 251 are mounted on the outward-facing surface 234 such that the sensor electronics 260 are relatively closer in proximity to the convex surface 224 than if they were mounted on the inward-facing surface 232.

III. Example Ophthalmic Electrochemical Analyte Sensor

Figure 3:
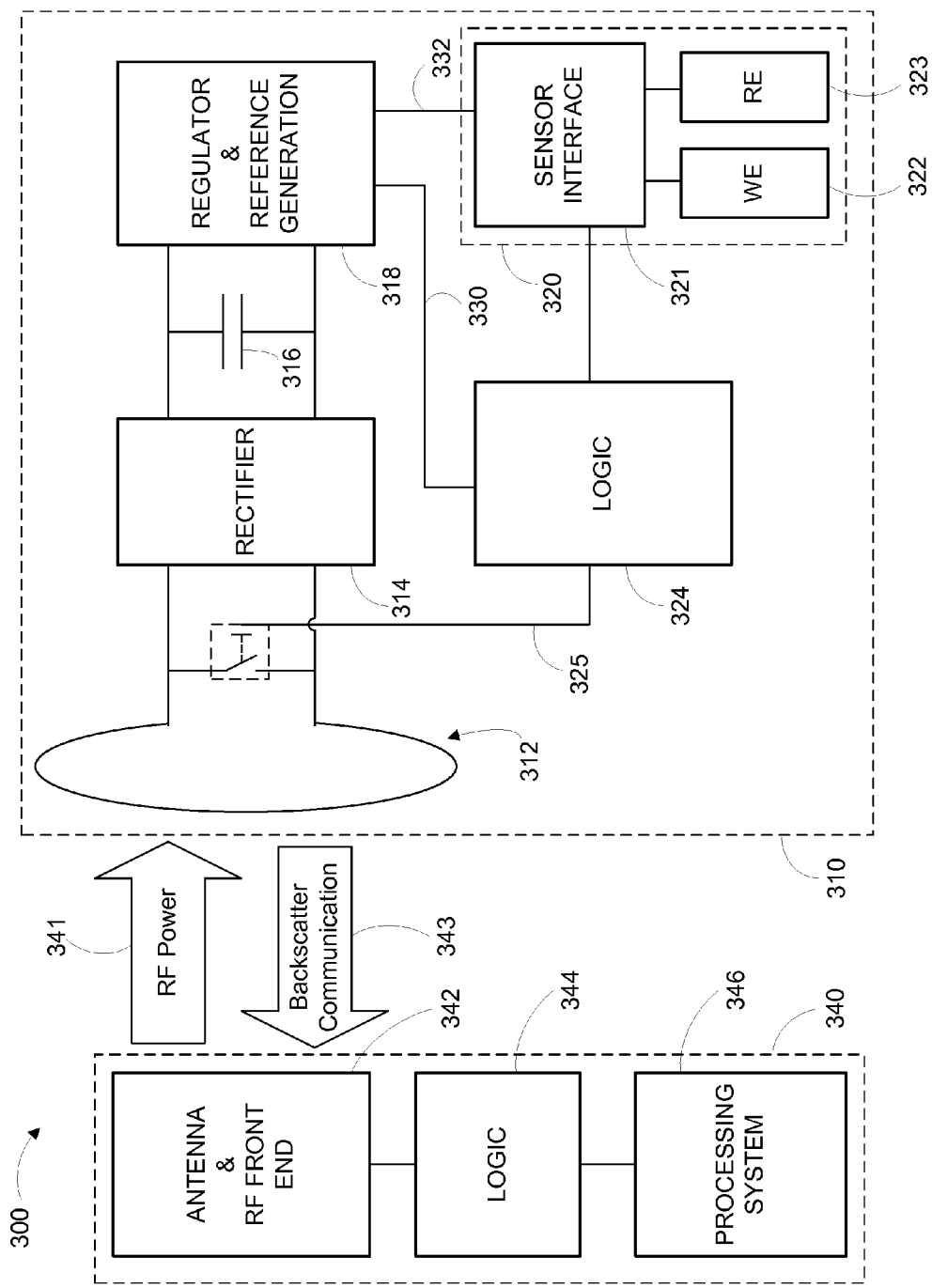
FIG. 3 is a functional block diagram of an example system for electrochemically measuring a tear film analyte concentration.

FIG. 3 is a functional block diagram of a system 300 for electrochemically measuring a tear film analyte concentration. The system 300 includes an eye-mountable device 310 with embedded electronic components powered by an external reader 340. The eye-mountable device 310 includes an antenna 312 for capturing radio frequency radiation 341 from the external reader 340. The eye-mountable device 310 includes a rectifier 314, an energy storage 316, and regulator 318 for generating power supply voltages 330, 332 to operate the embedded electronics. The eye-mountable device 310 includes an electrochemical sensor 320 with a working electrode 322 and a reference electrode 323 driven by a sensor interface 321. The eye-mountable device 310 includes hardware logic 324 for communicating results from the sensor 320 to the external reader 340 by modulating the impedance of the antenna 312. An impedance modulator 325 (shown symbolically as a switch in FIG. 3) can be used to modulate the antenna impedance according to instructions from the hardware logic 324. Similar to the eye-mountable devices 110, 210 discussed above in connection with FIGS. 1 and 2, the eye-mountable device 310 can include a mounting substrate embedded within a polymeric material configured to be mounted to an eye.

The electrochemical sensor 320 can be situated on a mounting surface of such a substrate proximate the surface of the eye (e.g., corresponding to the bio-interactive electronics 260 on the inward-facing side 232 of the substrate 230) to measure analyte concentration in a tear film layer interposed between the eye-mountable device 310 and the eye (e.g., the inner tear film layer 40 between the eye-mountable device 210 and the corneal surface 22). In some embodiments, however, an electrochemical sensor can be situated on a mounting surface of such a substrate distal the surface of the eye (e.g., corresponding to the outward-facing side 234 of the substrate 230) to measure analyte concentration in a tear film layer coating the exposed surface of the eye-mountable device 310 (e.g., the outer tear film layer 42 interposed between the convex surface 224 of the polymeric material 210 and the atmosphere and/or closed eyelids).

With reference to FIG. 3, the electrochemical sensor 320 measures analyte concentration by applying a voltage between the electrodes 322, 323 that is sufficient to cause products of the analyte catalyzed by the reagent to electrochemically react (e.g., a reduction and/or oxidization reaction) at the working electrode 322. The electrochemical reactions at the working electrode 322 generate an amperometric current that can be measured at the working electrode 322. The sensor interface 321 can, for example, apply a reduction voltage between the working electrode 322 and the reference electrode 323 to reduce products from the reagent-catalyzed analyte at the working electrode 322. Additionally or alternatively, the sensor interface 321 can apply an oxidization voltage between the working electrode 322 and the reference electrode 323 to oxidize the products from the reagent-catalyzed analyte at the working electrode 322. The sensor interface 321 measures the amperometric current and provides an output to the hardware logic 324. The sensor interface 321 can include, for example, a potentiostat connected to both electrodes 322, 323 to simultaneously apply a voltage between the working electrode 322 and the reference electrode 323 and measure the resulting amperometric current through the working electrode 322.

The rectifier 314, energy storage 316, and voltage regulator 318 operate to harvest energy from received radio frequency radiation 341. The radio frequency radiation 341 causes radio frequency electrical signals on leads of the antenna 312. The rectifier 314 is connected to the antenna leads and converts the radio frequency electrical signals to a DC voltage. The energy storage 316 (e.g., capacitor) is connected across the output of the rectifier 314 to filter out high frequency components of the DC voltage. The regulator 318 receives the filtered DC voltage and outputs both a digital supply voltage 330 to operate the hardware logic 324 and an analog supply voltage 332 to operate the electrochemical sensor 320. For example, the analog supply voltage can be a voltage used by the sensor interface 321 to apply a voltage between the sensor electrodes 322, 323 to generate an amperometric current. The digital supply voltage 330 can be a voltage suitable for driving digital logic circuitry, such as approximately 1.2 volts, approximately 3 volts, etc. Reception of the radio frequency radiation 341 from the external reader 340 (or another source, such as ambient radiation, etc.) causes the supply voltages 330, 332 to be supplied to the sensor 320 and hardware logic 324. While powered, the sensor 320 and hardware logic 324 are configured to generate and measure an amperometric current and communicate the results.

The sensor results can be communicated back to the external reader 340 via backscatter radiation 343 from the antenna 312. The hardware logic 324 receives the output current from the electrochemical sensor 320 and modulates (325) the impedance of the antenna 312 in accordance with the amperometric current measured by the sensor 320. The antenna impedance and/or change in antenna impedance is detected by the external reader 340 via the backscatter signal 343. The external reader 340 can include an antenna front end 342 and logic components 344 to decode the information indicated by the backscatter signal 343 and provide digital inputs to a processing system 346. The external reader 340 associates the backscatter signal 343 with the sensor result (e.g., via the processing system 346 according to a pre-programmed relationship associating impedance of the antenna 312 with output from the sensor 320). The processing system 346 can then store the indicated sensor results (e.g., tear film analyte concentration values) in a local memory and/or an external memory (e.g., by communicating with the external memory through a network).

In some embodiments, one or more of the features shown as separate functional blocks can be implemented ("packaged") on a single chip. For example, the eye-mountable device 310 can be implemented with the rectifier 314, energy storage 316, voltage regulator 318, sensor interface 321, and the hardware logic 324 packaged together in a single chip or controller module. Such a controller can have interconnects ("leads") connected to the loop antenna 312 and the sensor electrodes 322, 323. Such a controller operates to harvest energy received at the loop antenna 312, apply a voltage between the electrodes 322, 323 sufficient to develop an amperometric current, measure the amperometric current, and indicate the measured current via the antenna 312 (e.g., through the backscatter radiation 343).

Figure 4A:
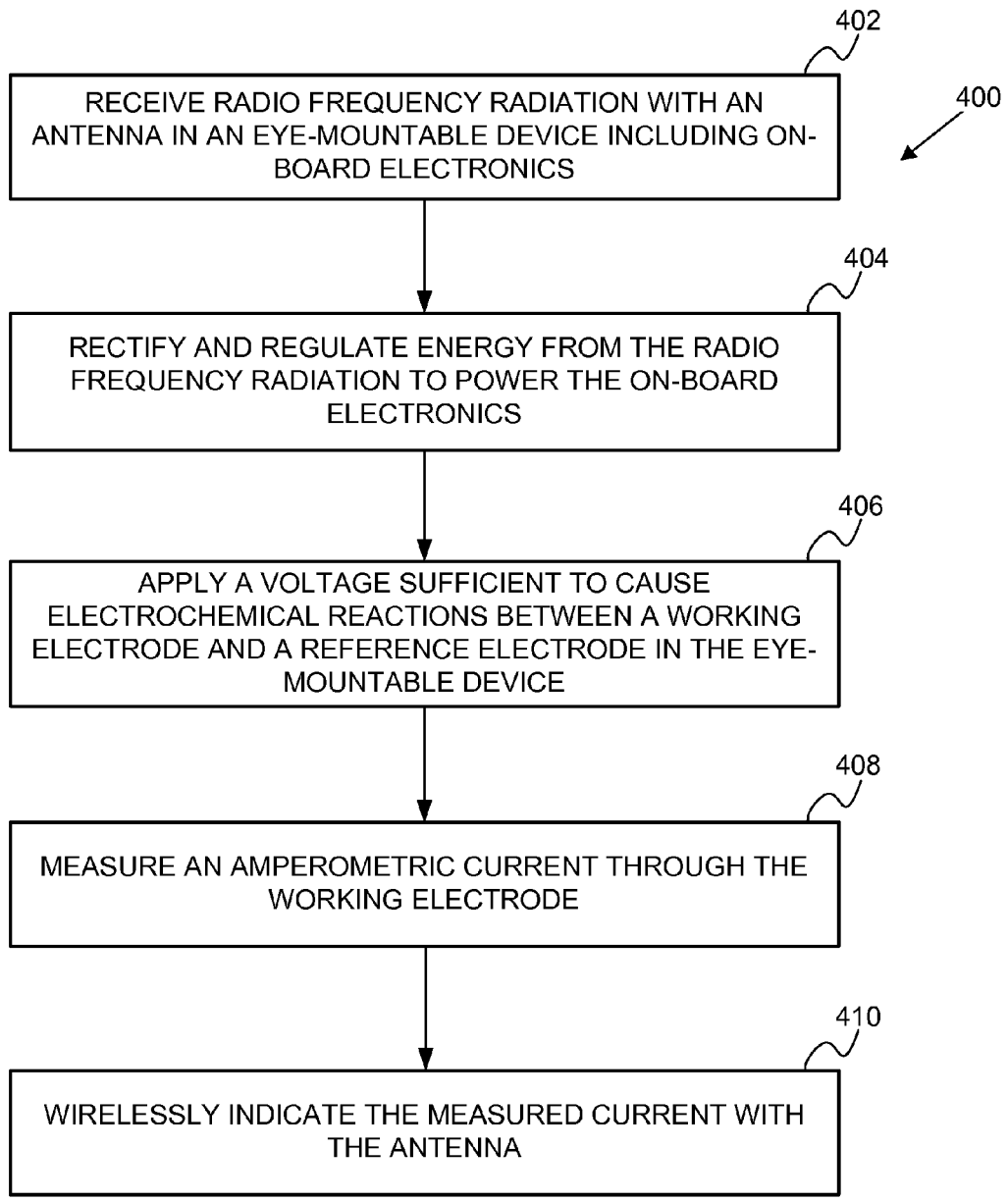
FIG. 4A is a flowchart of an example process for operating an amperometric sensor in an eye-mountable device to measure a tear film analyte concentration.

FIG. 4A is a flowchart of a process 400 for operating an amperometric sensor in an eye-mountable device to measure a tear film analyte concentration. Radio frequency radiation is received at an antenna in an eye-mountable device including an embedded electrochemical sensor (402). Electrical signals due to the received radiation are rectified and regulated to power the electrochemical sensor and associated controller (404). For example, a rectifier and/or regulator can be connected to the antenna leads to output a DC supply voltage for powering the electrochemical sensor and/or controller. A voltage sufficient to cause electrochemical reactions at the working electrode is applied between a working electrode and a reference electrode on the electrochemical sensor (406). An amperometric current is measured through the working electrode (408). For example, a potentiostat can apply a voltage between the working and reference electrodes while measuring the resulting amperometric current through the working electrode. The measured amperometric current is wirelessly indicated with the antenna (410). For example, backscatter radiation can be manipulated to indicate the sensor result by modulating the antenna impedance.

Figure 4B:
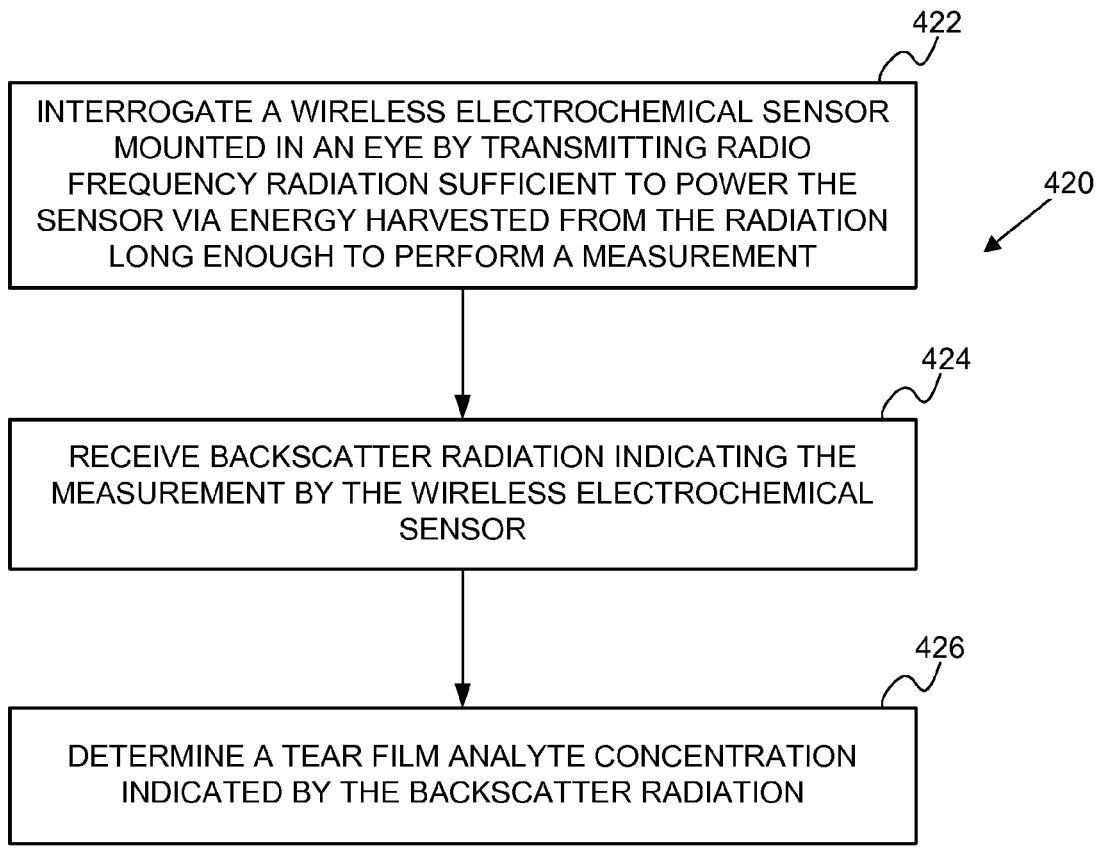
FIG. 4B is a flowchart of an example process for operating an external reader to interrogate an amperometric sensor in an eye-mountable device to measure a tear film analyte concentration.

FIG. 4B is a flowchart of a process 420 for operating an external reader to interrogate an amperometric sensor in an eye-mountable device to measure a tear film analyte concentration. Radio frequency radiation is transmitted to an electrochemical sensor mounted in an eye from the external reader (422). The transmitted radiation is sufficient to power the electrochemical sensor with energy from the radiation for long enough to perform a measurement and communicate the results (422). For example, the radio frequency radiation used to power the electrochemical sensor can be similar to the radiation 341 transmitted from the external reader 340 to the eye-mountable device 310 described in connection with FIG. 3 above. The external reader then receives backscatter radiation indicating the measurement by the electrochemical analyte sensor (424). For example, the backscatter radiation can be similar to the backscatter signals 343 sent from the eye-mountable device 310 to the external reader 340 described in connection with FIG. 3 above. The backscatter radiation received at the external reader is then associated with a tear film analyte concentration (426). In some cases, the analyte concentration values can be stored in the external reader memory (e.g., in the processing system 346) and/or a network-connected data storage.

For example, the sensor result (e.g., the measured amperometric current) can be encoded in the backscatter radiation by modulating the impedance of the backscattering antenna. The external reader can detect the antenna impedance and/or change in antenna impedance based on a frequency, amplitude, and/or phase shift in the backscatter radiation. The sensor result can then be extracted by associating the impedance value with the sensor result by reversing the encoding routine employed within the eye-mountable device. Thus, the reader can map a detected antenna impedance value to an amperometric current value. The amperometric current value is approximately proportionate to the tear film analyte concentration with a sensitivity (e.g., scaling factor) relating the amperometric current and the associated tear film analyte concentration. The sensitivity value can be determined in part according to empirically derived calibration factors, for example.

IV. Example Eye-Mountable Device Identification

Figure 5A:
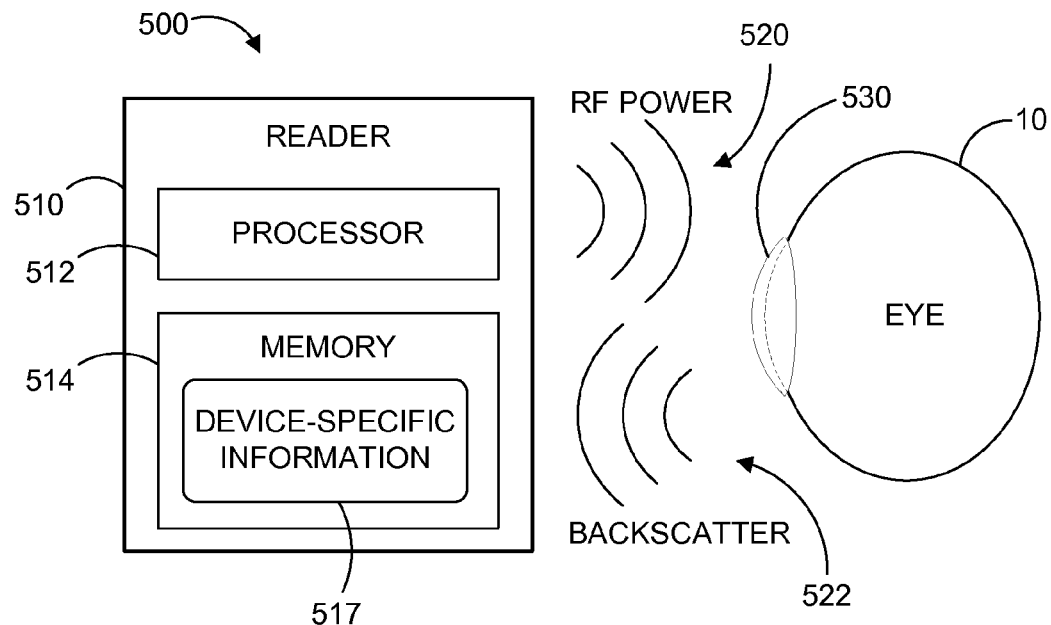
FIG. 5A is a block diagram of an example eye-mountable electronics platform in communication with an external reader.

FIG. 5A is a block diagram of a system 500 with an eye-mountable device 530 in communication with an external reader 510. The eye-mountable device 530 is configured to be contact-mounted over a corneal surface of an eye 10. The eye-mountable device 530 can operate to output an identification sequence and communicate the identification sequence to the external reader 510. Using the identification sequence, the reader 510 can then retrieve and/or store data specific to the particular device 530, such as configuration and/or calibration information. The reader 510 can differentiate between different eye-mountable devices, using the identification sequences from each, and associate device-specific data with each device. As such, the eye-mountable device 510 does not have any need for on-board programmable memory to store data. Instead, the reader 510 (or a database accessible by the reader 510) can store device-specific information in a manner that associates the stored information with the identification sequences of the eye-mountable device.

The external reader 510 includes a processing system 512 and a memory 514. The memory 514 can be a volatile and/or non-volatile computer readable media located in the reader 510 and/or in network communication with the reader 510. The memory 514 can be similar to, for example, the memory 182 in the external reader 180 discussed in connection with FIG. 1 above. The processing system 512 can be a computing system that executes software stored in the memory 514 to cause the system 500 to operate as described herein. The reader 510 may be incorporated into a wearable device, such as a device configured to be worn relatively near a user's eye, such as a hat, a headband, an earring, a pendant, eye glasses, etc. The reader 510 may also be incorporated into a watch, a mobile phone, or another personal electronics device.

In some examples, the reader 510 may obtain one or more measurements from sensor(s) on the eye-mountable device 530 (e.g., by intermittently transmitting a measurement signal to cause an electrochemical sensor included in the eye-mountable device 530 to obtain a measurement and communicate the results similar to the system described in connection with FIGS. 1-4). The external reader 510 can also include an antenna (not shown) for transmitting radio frequency radiation 520 to be harvested by the eye-mountable device 530. The external reader 510 can also receive information transmitted back to the reader by backscatter radiation 522. For example, the antenna impedance of the eye-mountable device 530 can be modulated in accordance with an identification sequence such that the backscatter radiation 522 indicates the identification sequence. The backscatter radiation 522 may also indicate sensor measurements, for example. The external reader 510 can also use the memory 514 to store indications of device-specific information 517 (e.g., amperometric current measurements) communicated from the eye-mountable device 530.

Figure 5B:
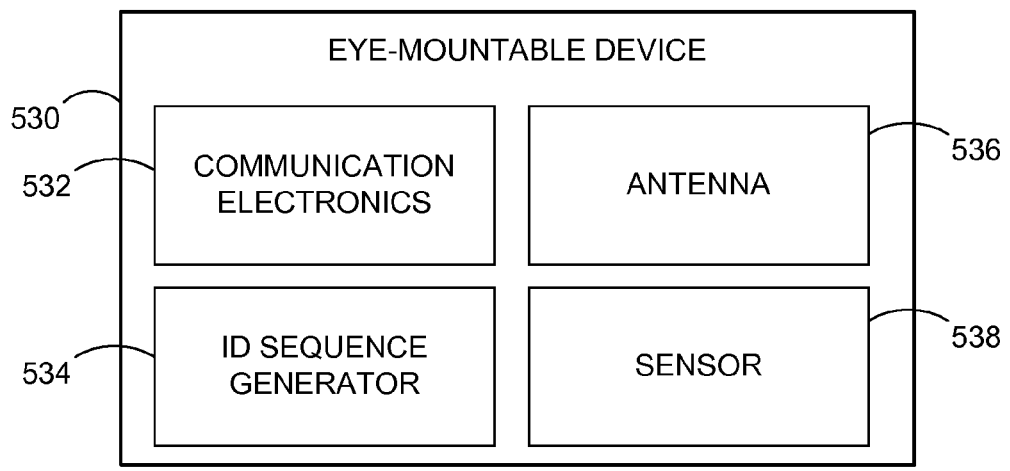
FIG. 5B is a block diagram of the example eye-mountable electronics platform described in connection with FIG. 5A.

FIG. 5B is a block diagram of the eye-mountable device 530 described in connection with FIG. 5A. The eye-mountable device 530 can include energy harvesting systems for harvesting energy from incident radiation 520 (and/or other sources) to power the device 530. For example, electronics for performing measurements and communicating a measurement result can be powered via energy harvesting circuitry.

The eye-mountable device 530 can include communication electronics 532, an identification sequence generator 534, an antenna 536, and a sensor 538 (or other bio-interactive electronics). The identification sequence generator 534 can be configured to output an identification sequence. The identification sequence can be a substantially unique series of values (e.g., a series of binary values) that provide a unique characterizing "fingerprint" for use in distinguishing the particular eye-mountable device 530 from others. The sequence generator 534 can be configured to repeatably (e.g., consistently) output the series in response to a prompt, such that the same particular device 530 can be consistently associated with the same identification sequence. For example, the identification sequence generator 534 can be a circuit that receives a prompt and outputs the identification sequence. The sequence generator 534 may be a circuit that is incorporated into a control chip of the eye-mountable device 530. In some examples, the identification sequence can be a serial number that is imprinted into the eye-mountable device 530 during a manufacturing process. For example, a circuit implementation of the sequence generator 534 can be customized, during manufacture, to output a substantially unique series of high/low values. Each ophthalmic device that is produced can then be assigned a different identification sequence, and the sequence generator circuits of each can be customized accordingly.

Additionally or alternatively, the sequence generator 534 can be configured to generate the identification sequence for the eye-mountable device 530 based on process variations in one or more circuit components. For example, a comparator circuit can be created that compares threshold voltages of two different transistors (or sets of transistors). The uncorrelated threshold voltage variations in such pairs can be amplified and digitized to create a sequence of binary values depending on the state of each comparator circuit. The individual binary state comparator circuits can each be formed from a comparator circuit (e.g., a latch circuit) with cross-coupled logic gates. Following a reset, each comparator circuit settles on one of two possible states depending on the random offset between the threshold voltages. Positive feedback in the cross-coupled arrangement amplifies the small variations to allow for readout. An array of many such circuits can then be used to create an identification sequence with a desired number of bits. Because the resulting identification sequence is based on random, uncorrelated variations in transistor threshold voltage (or other process variations in the die, etc.), the identification sequence may not be entirely unique (i.e., two different identification circuits may generate identical identification sequences). Moreover, such a sequence generator 534 that relies on random process variations may not consistently settle on the same output sequence. For example, comparisons between particularly close threshold voltages may not consistently settle on the same value, and some circuits may systematically change their output over time due to differential degradation of the compared circuit components. However, the probability of such ambiguities can be mitigated by using identification sequences with relatively greater word length (i.e., greater number of bits).

In an example, the sequence generator 534 can include multiple state circuits that are each configured to settle in one of multiple possible states, and each state circuit can then represent a bit (or multiple bits) in the substantially unique identification sequence. An example of such a state circuit can include a cross-coupled NOR gate. A pair of transistors can be arranged to cause the circuit to settle in one state or another depending on the difference in threshold voltage between the two. Each transistor has a gate terminal, a source terminal, and a drain terminal. The conductivity between the drain and source terminals is determined in part by the voltage applied across the gate and source terminals, with a gate-source voltage $V_{gs}$ exceeding a threshold $V_{th}$ resulting in a non-zero drain-source current $I_{ds}$. The pair of transistors can be connected with the gate of the first transistor connected to the source of the second transistor and the gate of the second transistor connected to the source of the first transistor. The drain of each transistor can be connected to a supply line (e.g., Vdd) and the source of each transistor can be connected to a ground line. The respective connections to the supply line and the ground line can each be made through a transistor driven by a reset line. Upon resetting the circuit the source terminals and cross-coupled gate terminals are all set low (e.g., set to ground).

During the reset to low voltage one of the two cross-coupled transistors becomes conductive before the other one (e.g., the one with the lower threshold voltage). Current through the transistor that becomes conductive first creates positive feedback to increase the gate-source voltage of the first conductive transistor while decreasing the conductivity of the second transistor, via the cross-coupled drain/gate connection. The drains of the two cross-coupled transistors then settle with one at a high voltage and one at a low voltage, depending on which of the two transistors has a higher threshold voltage. Because the threshold voltage $V_{th}$ is a function of variations in the physical properties of the transistor channel regions (e.g., charge carrier mobility, channel width and length, oxide conductance, etc.), either of the two states occur with roughly equal probability in a given cell due to uncorrelated process variations in the manufacture of the circuit. The drains of the two transistors (or one of them) thus represents an output state of the example state circuit that settles in one of multiple possible states based on random process variations in the manufacture of the state circuit. Other state circuits based on process variations in physical features in the constructed circuitry can also be employed; the above state circuit is described for example purposes only.

Upon receipt of an interrogation signal from the reader 510 (e.g., the radiation 520), the eye-mountable device 530 can power on (via harvested energy) and the sequence generator 534 can output the identification sequence. The communication electronics 532 can then use the antenna 536 to communicate an indication of the identification sequence back to the reader 510. For example, the communication electronics 532 may modulate the impedance of the antenna 536 in accordance with the identification sequence, so as to encode information indicative of the identification sequence in the backscatter radiation 522, which can then be decoded by the reader 510. The eye-mountable device 530 can also include measurement electronics configured to measure an amperometric current through the working electrode of the sensor 538 and communicate the measured amperometric current through the antenna 536 using the communication electronics 532.

Upon receipt of the backscatter radiation 522, the reader 510 can use the identification sequence to access device-specific information 517 in the memory 514. For example, the reader 510 may lookup configuration and/or calibration data for the device 530, a date of manufacture, production batch, shipment date, or expiration date of the device 530, any information regarding prior use of the device 530, an particular user associated with the device 530, etc. Such device-specific information 517 may be previously loaded to the memory 514 in connection with manufacture, calibration, testing, or prior use(s) of the device 530, for example. In addition, the reader 510 may supplement such device-specific information 517 with additional sensor readings, user preferences, etc., such that the additional information is associated with the identification sequence that identifies the particular device 530. Additionally or alternatively, the reader 510 may access device-specific information stored non-locally (e.g., a database stored on a server in communication with the reader 510).

Once accessed, the device-specific information 517 can then be used by the reader 510 to operate the eye-mountable device 530. For example, the reader 510 may use configuration data included in the device-specific information 517 to determine how often (or under what conditions) to query the eye-mountable device 530 for readings. Configuration data may also specify a desired amperometric current stabilization time for the electrochemical sensor 538, and the reader 510 may therefore be configured to instruct the eye-mountable device 530 to first apply a voltage across electrodes in the sensor 538 for a period while the amperometric current stabilizes (e.g., as the electrochemical reactions at the working electrode reach a steady state). Following the stabilization time, the reader 510 can then prompt the eye-mountable device 530 to measure the amperometric current and indicate the measured current via the backscatter radiation 522. Other device-specific operation preferences are also possible. Additionally or alternatively, the reader 510 may use calibration data to interpret sensor readings (i.e., amperometric current measurements). Such calibration data may include, for example, a sensitivity and/or offset to define a calibration curve that relates current measurements to analyte concentrations. An example of a calibration procedure and resulting calibration values associated therewith is described below in connection with FIGS. 7-8.

By storing device-specific information 517 off of the device, and mapping such information to the device using the substantially unique identification sequence output from the sequence generator 534, the device 530 does not require on-board programmable memory. As such, the memory-free device 530 does not store any user-specific information (e.g., prior sensor readings, etc.). Such a memory-free configuration thereby alleviates potential privacy concerns because user-specific information is stored on a platform suitable for incorporating data-protection routines, such as credentialed logins, encryption schemes, etc., which platform may be any combination of the reader 510 and/or external servers. Moreover, the memory-free configuration alleviates concerns over losing data stored in the device 530 in the event of losing the device (e.g., due the device 530 detaching from the eye 10). As such, the memory-free configuration described herein facilitates implementations in which the eye-mountable device 530 may be a disposable product, similar to a disposable contact lens employed in vision correction applications.

Figure 6A:
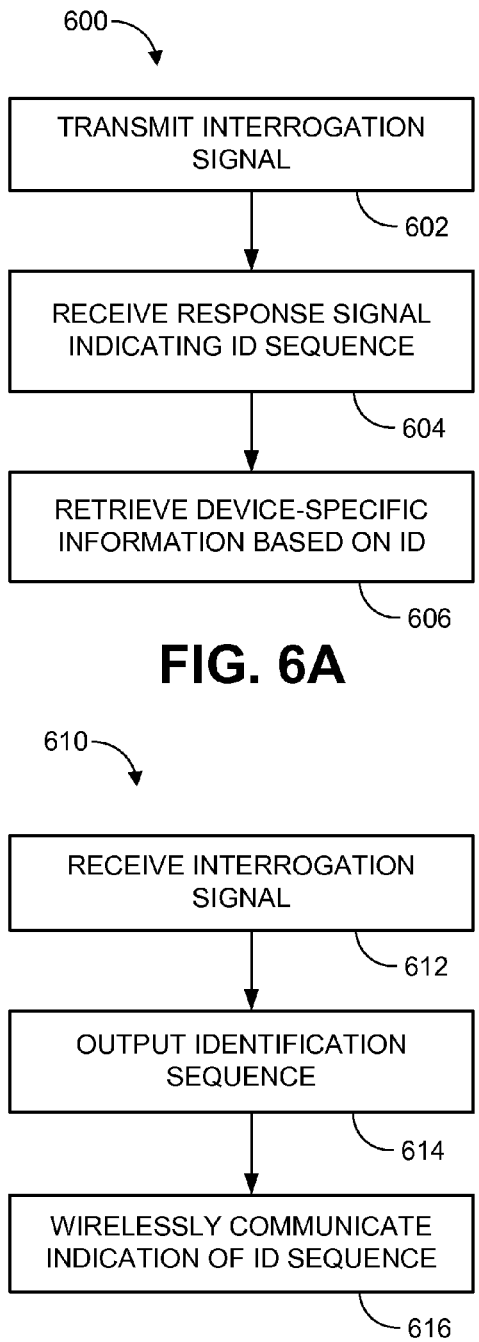
FIG. 6A is a flowchart of an example process for retrieving device-specific information based on an identification sequence for an eye-mountable device.
Figure 6B:
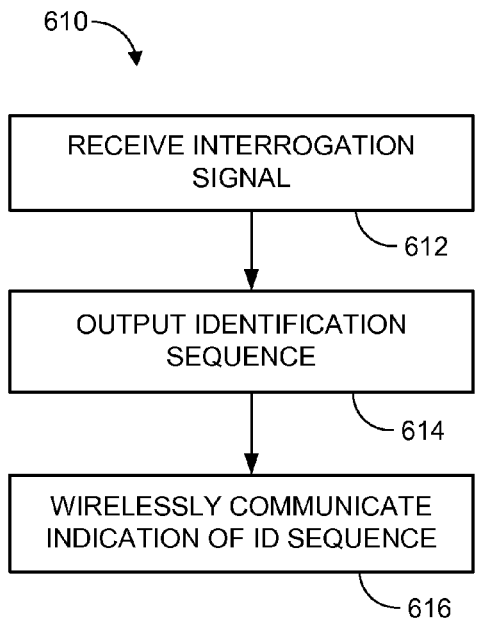
FIG. 6B is a flowchart of an example process for communicating an identification sequence from an eye-mountable device.
Figure 6C:
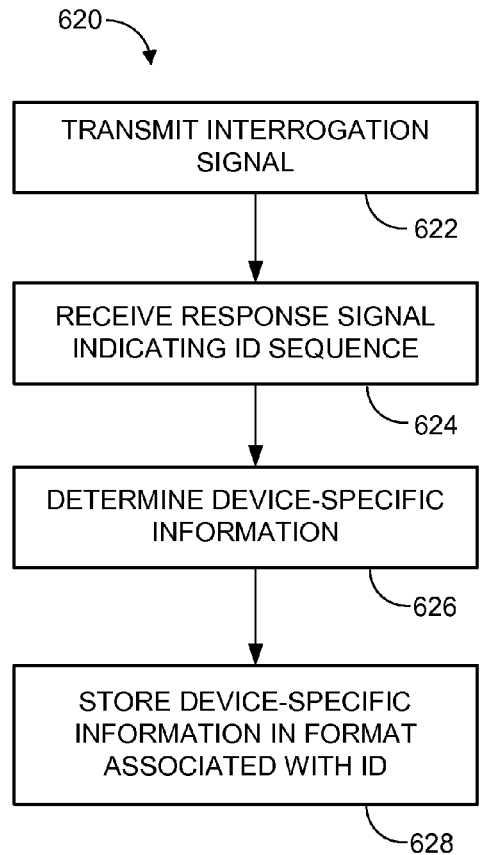
FIG. 6C is a flowchart of an example process for storing device-specific information for an eye-mountable device.

FIGS. 6A-6C illustrate various example processes that may be involved in associating device-specific information with a particular eye-mountable device according to an identification sequence output from the eye-mountable device. FIG. 6A is a process performed by a reader to obtain an identification sequence from an eye-mountable device and then retrieving device-specific information. FIG. 6B is a process performed by an eye-mountable device to communicate an identification sequence for the particular eye-mountable device in response to a query from a reader. FIG. 6C is a process performed by a reader to store device-specific information associated with a particular eye-mountable device by associating the information with the identification sequence for the particular device.

FIG. 6A is a flowchart of an example process 600 for retrieving device-specific information based on an identification sequence received from an eye-mountable device. The process 600 includes transmitting an interrogation signal to an eye-mountable device, at block 602. For example, the reader 510 may transmit the radiation 520 to the device 530. Upon receiving the interrogation signal, the eye-mountable device sends a response signal indicating of an identification sequence for the eye-mountable device. The device 530 may output the sequence from the generator 534 and modulating the antenna impedance to cause the backscatter radiation 522 to indicate the identifications sequence. The resulting response signal indicating the identification sequence is received, at block 604. For example, the reader 510 can receive the backscatter radiation 522, and the identification sequence can be decoded from the received backscatter. The identification sequence can then be used to retrieve device-specific information, at block 606. For example, the reader 510 can use the identification sequence to lookup device-specific configuration, calibration, origin, user, and/or prior usage information 517 in the memory 514 or in a database accessible via the reader 510.

FIG. 6B is a flowchart of an example process 610 for communicating an identification sequence from an eye-mountable device. The process 610 includes receiving an interrogation signal at an eye-mountable device, at block 612. For example, the eye-mountable device 530 can receive the radiation 520 from the reader 510, as described in connection with FIG. 5 above. In response to receiving the interrogation signal (612), the eye-mountable device can generate an identification sequence, at block 614. For example, the identification sequence can be output from the sequence generator 534, which may be a circuit configured to repeatably (e.g., consistently) output a sequence of bits to form the identification sequence. The identification sequence can be substantially unique, such that a particular eye-mountable device can be substantially unambiguously identified using its identification sequence. The identification sequence can be hard-coded into the sequence generator 534, similar to a serial number, or the identification sequence may be at least partially output according to one or more circuit components that are configured to settle at one of several possible states based on process variations between the components (e.g., uncorrelated variations in transistor threshold voltages, etc.). The eye-mountable device can then use the antenna to wirelessly communicate an indication of the identification sequence, at block 616. For example, the communication electronics 532 may modulate the impedance of the antenna 536 so as to encode an indication of the identification sequence in the backscatter radiation 522 (e.g., according to modulations in the amplitude, phase, frequency, etc. of the backscatter).

FIG. 6C is a flowchart of an example process 620 for storing device-specific information for an eye-mountable device. The process 620 includes transmitting an interrogation signal to an eye-mountable device, at block 622, and receiving the resulting response signal indicating the identification sequence is received, at block 624. Blocks 622 and 624 are similar to blocks 602 and 604 of the process 600 and cause the reader to obtain an identification sequence for the eye-mountable device. The reader can then determine device-specific information for the eye-mountable device, at block 626. For example, the reader 510 may obtain a sensor measurement from the eye-mountable device 530 and determine a corresponding analyte concentration. In another example, the reader 510 may perform a calibration on the amperometric sensor in the eye-mountable device 530 and determine one or more calibration values based on such calibration. In another example, the reader 510 may determine a user to associate with the particular eye-mountable device 530 (e.g., via inputs to a user interface of the reader 510 or according to predetermined settings, etc.). Other examples of device-specific information may be determined by the reader 510. Once such device-specific information is determined, the information can be stored in a format that associates the device-specific information with the identification sequence, at block 628. As such, the device-specific information can be recalled (e.g., accessed) using the identification sequence to lookup the device-specific information for the particular eye-mountable device 510. The device-specific information can be stored in the memory 514 of the reader 510 (e.g., the device-specific information 517) and/or in a database accessible to the reader 510 (e.g., in communication via a network).

V. Example Application: Calibration Information

In some examples, device-specific information that can be associated with a particular eye-mountable device using its identification sequence can include calibration information for one or more sensors included on the device (e.g., the biosensor 162 described in connection with FIG. 1). Such sensors may include, for example, electrochemical analyte sensors, temperature sensors, light sensors (e.g., photocells), corneal pressure sensors (and/or strain sensors), acceleration sensors (accelerometers), and other sensors for obtaining measurements. In some examples, an eye-mountable device may be equipped with sensors for monitoring ophthalmic conditions, such as sensors for measuring corneal shape and/or thickness, for example. Such sensors may also be associated with calibration information to correct for systematic and/or random variations in sensor output in order to map measurements obtained by the sensor to physical quantities. FIGS. 7 and 8 describe an example in which an eye-mountable device with an electrochemical analyte sensor is associated with calibration information for the analyte sensor using its identification sequence. However, it is noted that an eye-mountable device may additionally or alternatively have other sensors (e.g., temperature, light, pressure, etc.) and calibration information may be associated with the eye-mountable device using its identification sequence.

Figure 7A:
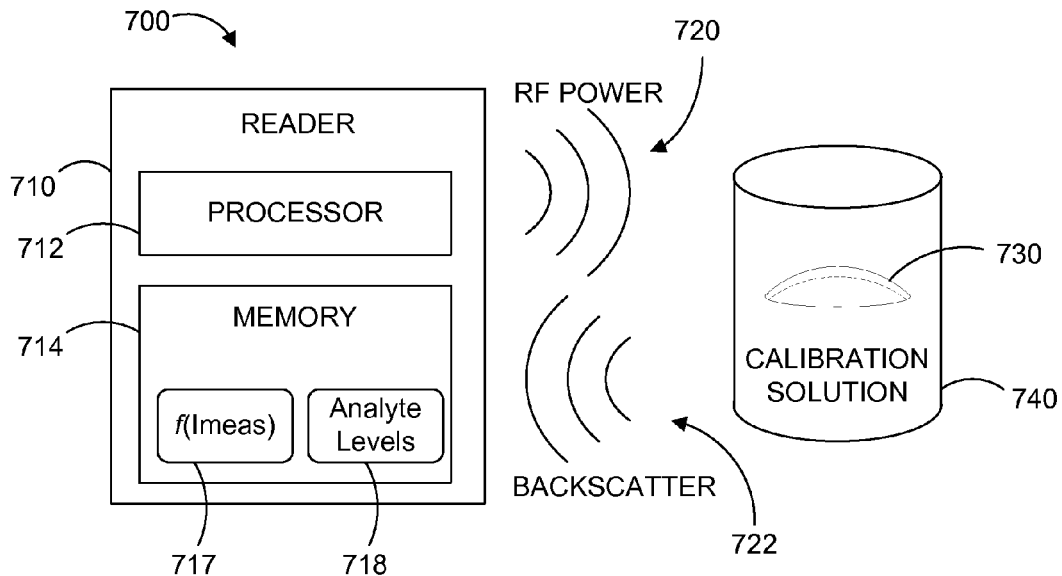
FIG. 7A is a block diagram of an example ophthalmic analyte sensor undergoing calibration.

FIG. 7A is a block diagram of an example ophthalmic analyte sensor undergoing calibration. The eye-mountable device 730 can be similar to the eye-mountable devices 110, 210, 310, 530 discussed above in connection with FIGS. 1-6 and includes an electrochemical sensor embedded within a polymeric material configured to be contact-mounted to an eye. The electrochemical sensor includes a working electrode and a reference electrode and can be operated to generate an amperometric current indicating the concentration of an analyte of interest (e.g., glucose). A reagent layer is localized near the working electrode to sensitize the electrochemical sensor to the analyte of interest. The eye-mountable device 730 is powered to measure an analyte concentration by harvesting energy from incident radio frequency radiation 720. The eye-mountable device 730 wirelessly communicates the sensor results to an external reader 710 by backscatter radiation 722.

The reader 710 includes a processing system 712 and a memory 714 storing calibration data 717 and sensor results data 718. The calibration data 717 is used to map sensor measurements to analyte concentration levels. The calibration data 717 can include, for example, coefficients in a function relating sensor measurements to analyte concentrations (e.g., slope and intercept values of a linear relationship), a look-up table relating sensor readings to analyte concentration levels, another indication for used to map sensor measurements to analyte concentration levels, etc. The sensor results data 718 can include one or more previous tear film analyte concentration levels measured with the system 700. Additionally or alternatively, the sensor results data 78 can also include raw sensor outputs (e.g., amperometric current values).

The reader 710 may also include a user input device to indicate to the reader 710 that a calibration procedure is being performed. For example, the user input may signal that sensor measurements are being obtained using a solution with a known analyte concentration, and cause the reader 710 to enter a calibration mode. The user input may also be used to indicate to the reader 710 when the calibration is complete, so the reader 710 can return to a measurement mode for interpreting subsequent in-vitro measurements. Such a user input may also indicate the concentrations of calibration solutions (if applicable) to allow the reader 710 to interpret amperometric sensor measurements obtained during the calibration. A wireless connection or other data communication technique may also be used to alert the reader 710 that a calibration procedure is being performed.

During calibration, the system 700 updates the calibration data 717 stored in the memory 714 in accordance with a calibration-solution sensor reading. The eye-mountable device 730 is exposed to a calibration solution 740 with a known analyte concentration. The eye-mountable device 730 can be exposed to the calibration solution 740 in a manner that allows the embedded electrochemical analyte sensor to sense the analyte concentration of the calibration solution 740. For example, the eye-mountable analyte sensor 730 can be submerged in a vessel filled with the calibration solution 740, a drop of calibration solution can be placed on the exterior of the eye-mountable device (e.g., convex surface) of the eye-mountable device 730, etc.

The reader 710 obtains a calibration measurement from the eye-mountable device 730 by sending a measurement signal (e.g., the radiation 720). The reader 710 interrogates the eye-mountable device 730 to obtain a reading in a manner similar to the process 420 discussed in connection with FIG. 4B above. For example, the reader 710 can radiate radio frequency radiation 720 to power the eye-mountable device 730 while the eye-mountable device applies voltage across sensor electrodes and measures an amperometric current at the working electrode. The reader 710 can then receive backscatter radiation 722 indicating the measurement result.

The calibration-solution sensor result is used to update (and/or create) the calibration data 717 in the memory 714. The calibration data 717 can be updated by determining a functional relationship for mapping sensor measurements to analyte concentrations. Such a functional relationship can be based entirely on the calibration-solution sensor result. The newly determined functional relationship can additionally or alternatively be based on the calibration-solution sensor result in combination with previously measured calibration data points and/or other assumptions or predictions, etc. The stored calibration data 717 can include one or more calibration value(s) indicative of the determined relationship between sensor measurements and analyte concentrations (e.g., slope and intercept of a linear relationship). It is noted that the present disclosure applies to calibrations of relationships other than linear relationships, such as higher-order polynomial functional relationships, a look-up table, etc.

Figure 7B:
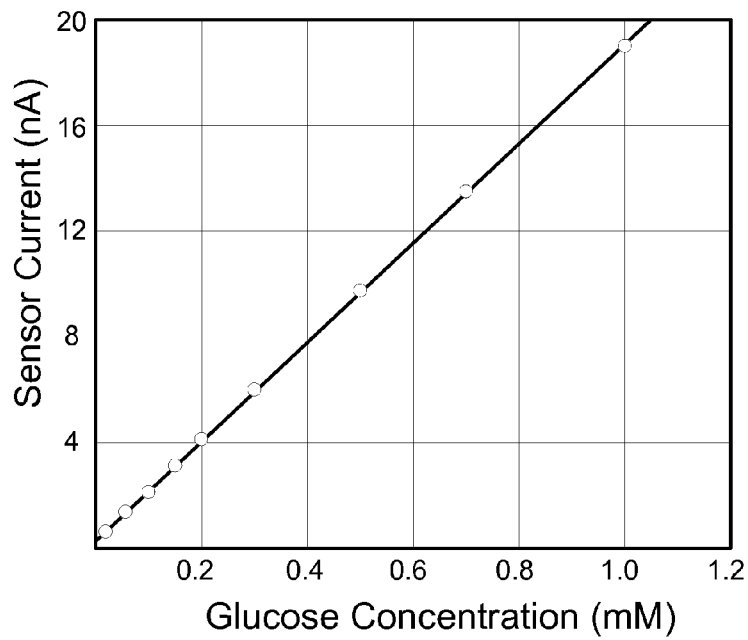
FIG. 7B is a graph showing example amperometric current values for a range of glucose concentrations.

FIG. 7B is a graph showing example amperometric current values for a range of glucose concentrations. The amperometric current values correspond to measurements by an electrochemical sensor configured to sense glucose. The electrochemical sensor includes a working electrode and a reference electrode driven by a controller, such as a potentiostat. For example, a potentiostat can apply a voltage between the electrodes sufficient to induce electrochemical reactions at the working electrode and thereby generate an amperometric current while measuring the amperometric current. Glucose oxidase is localized near the working electrode to sensitize the sensor to glucose. The glucose oxidase catalyzes glucose to create hydrogen peroxide, which is then oxidized at the working electrode to generate the amperometric current. Human tear film glucose concentrations can range from about 0 millimolar to about 1 millimolar (mM). To calibrate the electrochemical glucose sensor current response over the clinically relevant range, calibration solutions with known glucose concentrations can be prepared between about 0 mM and about 1 mM, and sensor readings can be obtained while the sensor is exposed to each of the calibration solutions, similar to the calibration mode operation of the system 700 described above in connection with FIG. 7A. For example, the external reader 710 can obtain sensor readings by interrogating the eye-mountable device 630 to perform a measurement while the eye-mountable device 730 is exposed to a calibrated solution. The external reader 710 can then wirelessly receive the sensor result similar to the process. Example results from such a procedure are shown as circles in the graph in FIG. 7B and are listed in the table below.

| Glucose Concentration [mM] | Measured Current [nA] |
|---|---|
| 0.02 | 0.60 |
| 0.06 | 1.36 |
| 0.10 | 2.13 |
| 0.15 | 3.12 |
| 0.20 | 4.04 |
| 0.30 | 6.01 |
| 0.50 | 9.74 |
| 0.70 | 13.4 |
| 1.00 | 19.0 |

The example calibration data shows a substantially linear relationship between glucose concentration and measured current. The trend line included in the graph in FIG. 7B defines a relationship relating sensor current and glucose concentration over the clinically relevant range of about 0 mM to about 1 mM. The trend line relates the measured currents to the calibrated glucose concentrations. The trend line can be used to determine analyte concentration as a function of sensor current, which can then be used to relate subsequent amperometric current measurements to analyte concentrations. For example, while obtaining in-vitro measurements (similar to the arrangement of the system 500 described in connection with FIG. 5A), the external reader 710 can be programmed to map amperometric currents to corresponding analyte concentrations according to a functional relationship dependent on the amperometric current. That is, a functional relationship can be determined from the calibration data of the form:

$$AC = f(\text{Imeas}),$$

where AC is the analyte concentration, Imeas is the measured amperometric current, and $f$ represents the functional form stored in the external reader 710 as the calibration data 717. The determined analyte concentration can then be stored in the sensor measurement data 718 of the memory 714.

In some embodiments, one or more calibration data points (e.g., a measured sensor result for a known analyte concentration) can be used to determine the functional form of a relationship relating measured current and analyte concentration. For example, any two such calibration data points can be used to solve for coefficients in a first-degree polynomial (e.g., a linear function) by fitting a line to the data points. Additional calibration data points can be used to determine a functional relationship based on a higher order polynomial (e.g., a quadratic functional relationship, etc.). Additionally or alternatively, the functional relationship determined by calibration data can be determined according to a minimization technique (e.g., minimization of $\chi^2$, etc.) where there are a greater number of calibration data points than degrees of freedom in the functional relationship.

Moreover, in some embodiments, a look-up table listing sensor readings and corresponding analyte concentration levels can be used to map sensor readings to analyte concentrations. For example, entries in such a look-up table can be interpolated to associate a tear film sensor reading with an analyte concentration. In some embodiments, a calibration can be performed on one or more of a batch of eye-mountable electrochemical sensors manufactured under similar conditions, and the derived calibrated functional relationship can be loaded to each such sensor in the batch.

The functional form of the relationship relating measured amperometric currents and analyte concentrations can be set according to an empirically derived calibration data set, according behavior of similar devices, and/or according to theoretical predictions. For example, an eye-mountable electrochemical analyte sensor can be calibrated in connection with its manufacturing process by obtaining sensor outputs (e.g., amperometric currents) while the sensor is exposed to one or more solutions with known analyte concentrations. Regardless of the source of such calibration information, one or more calibration values indicating the determined mapping (e.g., functional relationship) can then be stored in a database and/or in the memory 714 in a manner that associates the calibration information 717 with a substantially unique identification sequence of the eye-mountable device 730.

Figures 8A, 8B:
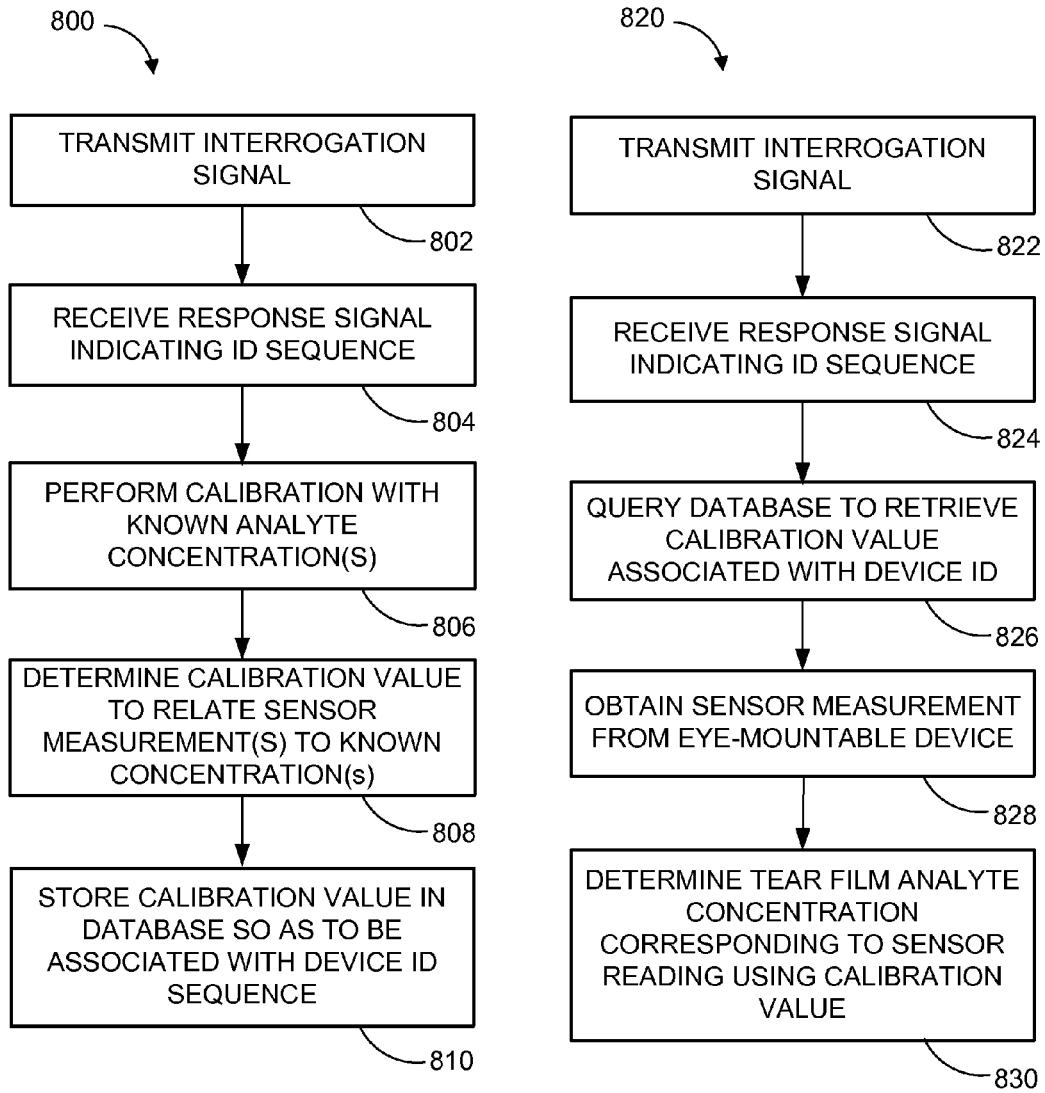
FIG. 8A is a flowchart of an example process for calibrating an ophthalmic analyte sensor.
FIG. 8B is a flowchart of an example process for interpreting a sensor reading using a predetermined calibration value.

FIG. 8A is a flowchart of an example process 800 for calibrating an ophthalmic analyte sensor. The process 800 includes transmitting an interrogation signal to an eye-mountable device, at block 802, and receiving the resulting response signal indicating the identification sequence is received, at block 804. Blocks 802 and 804 are similar to blocks 602 and 604 of the process 600 and cause the reader to obtain an identification sequence for the eye-mountable device. A calibration routine is then performed, at block 806. For example, the calibration routine may include exposing the eye-mountable device 730 to the calibration solution 740 with known analyte concentration (or multiple calibration solutions with different analyte concentrations) and obtaining sensor readings while the device 730 is so exposed. The sensor measurements obtained during calibration can then be used to determine a calibration value that relates the sensor measurements to the known analyte concentrations used during the calibration, at block 808. For example, the calibration value may indicate a functional relationship for mapping amperometric current measurements to analyte concentrations. The calibration routine and determination of suitable calibration values can be similar to the calibration procedure described above in connection with FIG. 7A. The determined calibration value can then be stored in a database so as to be associated with the device's identification sequence, at block 810.

FIG. 8B is a flowchart of an example process 820 for interpreting a sensor reading using a predetermined calibration value. The process 820 includes transmitting an interrogation signal to an eye-mountable device, at block 822, and receiving the resulting response signal indicating the identification sequence is received at block 824. Blocks 822 and 824 are similar to blocks 602 and 604 of the process 600 and cause the reader to obtain an identification sequence for the eye-mountable device. Upon determining the identification sequence for the sensor equipped eye-mountable device, the reader can query a database to retrieve calibration information associated with the identification sequence, at block 826. For example, the reader 710 can lookup previously stored calibration value(s) that define a mapping between amperometric sensor measurements and analyte concentrations (e.g., coefficients in a functional relationship, entries in a lookup table, etc.). The calibration value(s) retrieved in block 826 can be stored in the memory 714 of the reader 710, or in a networked database in communication with the reader 710. An amperometric sensor measurement is obtained from the eye-mountable device, at block 828. For example, the reader 710 can transmit radiation to the sensor-equipped eye-mountable device 730, the eye-mountable can then perform a measurement and modulate backscatter radiation to indicate the measured current, and the reader 710 can receive the indication of the measurement. The reader can then use the calibration value retrieved from the database to determine the tear film analyte concentration corresponding to the sensor measurement, at block 830. For example, the reader 710 can evaluate the measured amperometric current according to a functional relationship defined by the calibration values, so as to map the measurement to an analyte concentration.

The example processes 800 and 820 of FIGS. 8A and 8B allow for a particular sensor-equipped eye-mountable device to undergo a calibration procedure, and the results of the calibration to be used to interpret subsequent measurements with the sensor. Storing the calibration information in a manner that is associated with the particular eye-mountable device's identification sequence allows for the calibration information (e.g., calibration value(s)) for the particular eye-mountable device to be retrieved during a subsequent measurement using the eye-mountable device without storing such information on the eye-mountable device (e.g., on programmable memory). On the contrary, the eye-mountable device may lack any programmable memory. Instead, any device-specific information can be associated with the identification sequence for the eye-mountable device, and then retrieved subsequently using the identification sequence. Because the eye-mountable device is configured to communicate its identification sequence in response to an interrogation signal, the systems described herein allow for a reader to obtain a particular device's identification sequence, and then retrieve any device-specific for the particular device using the identification sequence. While the example systems and processes described herein disclose sensor calibration information as one example of device-specific information, other examples are possible, such as device manufacture information (e.g., production batch identification, production date, shipment date, expiration date, etc.), associated user information (e.g., user identity, user configuration/profile information, such as number or frequency of measurements to perform for the particular user, predetermined alert levels, etc.), and/or device usage history (e.g., historical sensor measurements, time since last usage, time since last calibration, etc.). Other examples of device-specific information are also possible as the examples provided herein are generally included by way of example and not limitation.

Moreover, it is particularly noted that while the electronics platform is described herein by way of example as an eye-mountable device or an ophthalmic device, it is noted that the disclosed systems and techniques for memory-free configurations of electronics platforms can be applied in other contexts as well. For example, contexts in which bio-sensors are operated with low power budgets (e.g., via harvested energy from radiated sources) or are constrained to small form factors (e.g., implantable bio-sensors or other electronics platforms) may employ the systems and processes described herein to associate device-specific information with particular electronics platforms based on a substantially unique identification sequence output from the electronics platform. In one example, an implantable medical device that includes a bio-sensor may be encapsulated in biocompatible material and implanted within a host. The implantable medical device may include a circuit configured to output a substantially unique identification sequence (e.g., an array of individual state circuits that consistently settle in one of several possible states according to process variations in the construction of the circuit). Reading and/or control devices can communicate with the implantable medical device to determine the identification sequence and then use the identification sequence to access device-specific information for the device. For example, the reader can query a database using the identification sequence and retrieve and/or store device-specific information. The configurations disclosed herein that are free of programmable memory simultaneously can address spatial constraints in small form factor applications, power budget constraints in low power applications, and/or data security concerns for devices capable of gathering private information.

For example, in some embodiments, the electronics platform may include a body-mountable device, such as a tooth-mountable device. In some embodiments, the tooth-mountable device may take the form of or be similar in form to the eye-mountable device 110, the eye-mountable device 310, and/or the eye-mountable device 530. For instance, the tooth-mountable device may include a biocompatible polymeric material or a transparent polymer that is the same or similar to any of the polymeric materials or transparent polymers described herein and a substrate or a structure that is the same or similar to any of the substrates or structures described herein. In such an arrangement, the tooth-mountable device may be configured to detect at least one analyte in a fluid (e.g., saliva) of a user wearing the tooth-mountable device.

Moreover, in some embodiments, a body-mountable device may comprise a skin-mountable device. In some embodiments, the skin-mountable device may take the form of or be similar in form to the eye-mountable device 110, the eye-mountable device 310, and/or the eye-mountable device 530. For instance, the skin-mountable device may include a biocompatible polymeric material or a transparent polymer that is the same or similar to any of the polymeric materials or transparent polymers described herein and a substrate or a structure that is the same or similar to any of the substrates or structures described herein. In such an arrangement, the skin-mountable device may be configured to detect at least one analyte in a fluid (e.g., perspiration, blood, etc.) of a user wearing the skin-mountable device.

Further, some embodiments of the systems and techniques disclosed herein may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Moreover, embodiments that involve information related to a person or a device of a person may include privacy controls. Such privacy controls may include, for example, anonymization of device identifiers, transparency regarding collection/use of information, and user controls including functionality that enables a user to modify and/or delete information relating to the user's use of the device.

Further, in situations in which embodiments discussed herein collect personal information about users, or may make use of personal information, the users may be provided with an opportunity to control whether programs or features collect user information (e.g., information about a user's medical history, social network, social actions or activities, profession, a user's preferences, a user's current location, etc.), or to control whether and/or how to receive content from a content server that may be more relevant to the user. In addition, certain data may be treated in one or more ways before it is stored or used, so that personally identifiable information is removed. For example, a user's identity may be treated so that no personally identifiable information can be determined for the user. Thus, the user may have control over how information is collected about the user and/or used by a content server.

Figure 9:
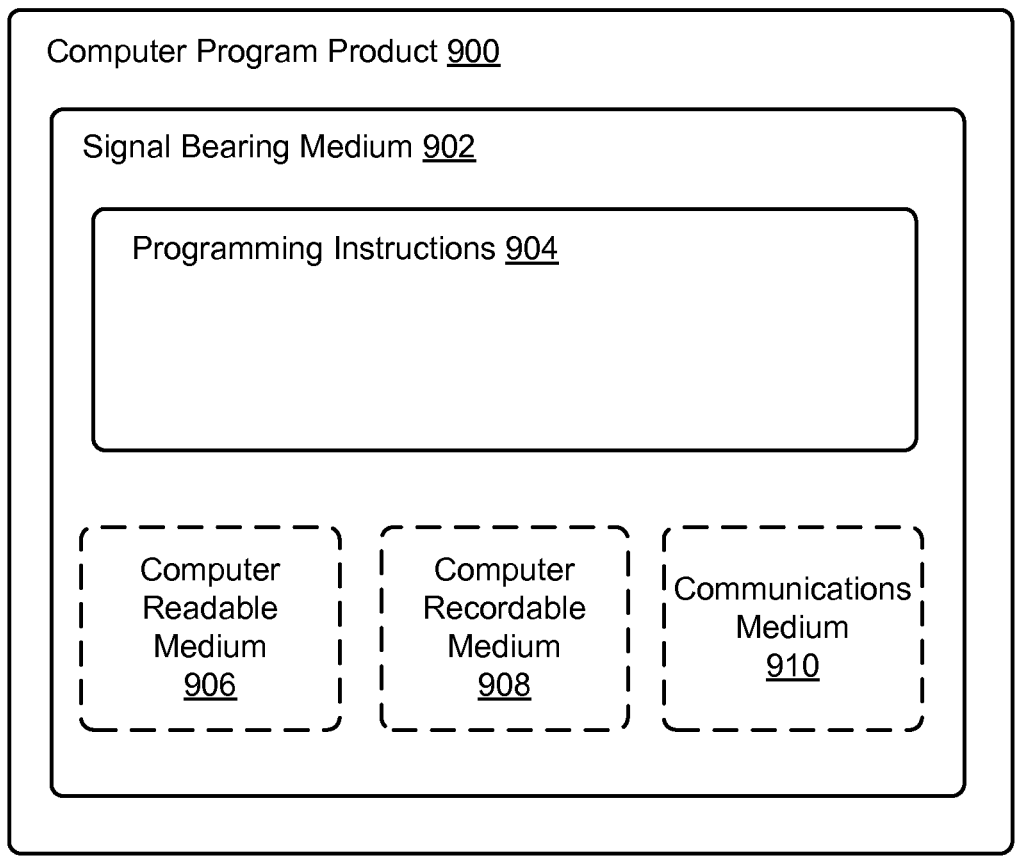
FIG. 9 depicts a computer-readable medium configured according to an example embodiment.

FIG. 9 depicts a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed techniques can be implemented by computer program instructions encoded on a non-transitory computer-readable storage media in a machine-readable format, or on other non-transitory media or articles of manufacture (e.g., the instructions 184 stored on the memory storage 182 of the external reader 180 of the system 100 or instructions stored on the memory 514 of the reader 510 of the system 500). FIG. 9 is a schematic illustrating a conceptual partial view of an example computer program product that includes a computer program for executing a computer process on a computing device, arranged according to at least some embodiments presented herein.

In one embodiment, the example computer program product 900 is provided using a signal bearing medium 902. The signal bearing medium 902 may include one or more programming instructions 904 that, when executed by one or more processors may provide functionality or portions of the functionality described above with respect to FIGS. 1-8. In some examples, the signal bearing medium 902 can be a non-transitory computer-readable medium 906, such as, but not limited to, a hard disk drive, a Compact Disc (CD), a Digital Video Disk (DVD), a digital tape, memory, etc. In some implementations, the signal bearing medium 902 can be a computer recordable medium 908, such as, but not limited to, memory, read/write (R/W) CDs, R/W DVDs, etc.

In some implementations, the signal bearing medium 902 can be a communications medium 910, such as, but not limited to, a digital and/or an analog communication medium (e.g., a fiber optic cable, a waveguide, a wired communications link, a wireless communication link, etc.). Thus, for example, the signal bearing medium 902 can be conveyed by a wireless form of the communications medium 910.

The one or more programming instructions 904 can be, for example, computer executable and/or logic implemented instructions. In some examples, a computing device such as the processor-equipped external reader 180 of FIG. 1 is configured to provide various operations, functions, or actions in response to the programming instructions 904 conveyed to the computing device by one or more of the computer readable medium 906, the computer recordable medium 908, and/or the communications medium 910.

The non-transitory computer readable medium 906 can also be distributed among multiple data storage elements, which could be remotely located from each other. The computing device that executes some or all of the stored instructions could be an external reader, such as the reader 180 illustrated in FIG. 1, or another mobile computing platform, such as a smartphone, tablet device, personal computer, etc. Alternatively, the computing device that executes some or all of the stored instructions could be remotely located computer system, such as a server.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. An eye-mountable device comprising:
a transparent polymeric material having a concave surface and a convex surface, wherein the concave surface removably mounts over a corneal surface and the convex surface is compatible with eyelid motion when the concave surface is so mounted;
a substrate at least partially embedded within the transparent polymeric material;
an antenna disposed on the substrate;
at least one sensor;
a sequence generator that dynamically generates a substantially unique identification sequence, wherein the substantially unique identification sequence is based on process variations in components of the sequence generator; and
a controller electrically connected to the antenna, wherein the controller: (i) receives an indication of an interrogation signal via the antenna, (ii) responsive to the interrogation signal, outputs the substantially unique identification sequence, (iii) uses the antenna to communicate the substantially unique identification sequence, (iv) responsive to communicating the substantially unique identification sequence, uses the antenna to receive an indication of device-specific information associated with the eye-mountable device, wherein the device-specific information is a response to said communicating of the substantially unique identification sequence and the device-specific information comprises user-specific information for operating the eye-mountable device, and (v) operates the at least one sensor in accordance with the user-specific information.

2. The eye-mountable device according to claim 1, wherein the sequence generator includes one or more state circuits that output one of multiple possible state outputs based on a difference between one or more circuit components in the one or more state circuits, and wherein the substantially unique identification sequence is based at least in part on the outputs of the one or more state circuits.

3. The eye-mountable device according to claim 1, wherein the sequence generator includes one or more comparator circuits that output a binary state value based on a comparison between an output of circuit components in the one or more comparator circuits, and wherein the substantially unique identification sequence is based at least in part on the binary state value.

4. The eye-mountable device according to claim 1,
wherein the controller uses the antenna to indicate a measurement obtained based on the operation of the at least one sensor in accordance with the user-specific information.

5. The eye-mountable device according to claim 4, wherein the at least one sensor includes: an electrochemical analyte sensor, a temperature sensor, a light sensor, a pressure sensor, or an acceleration sensor.

6. The eye-mountable device according to claim 1,
wherein the at least one sensor includes an electrochemical sensor disposed on the substrate and including: (i) a working electrode, and (ii) a reference electrode adjacent the working electrode, and
wherein the controller: (i) applies a voltage between the working electrode and the reference electrode sufficient to generate an amperometric current related to a concentration of an analyte in a fluid to which the eye-mountable device is exposed, (ii) measures the amperometric current, and (iii) uses the antenna to indicate the measured amperometric current.

7. The eye-mountable device according to claim 1, further comprising:
energy-harvesting circuitry that supplies power to operate the eye-mountable device via radiation received at the antenna.

8. The eye-mountable device according to claim 1, wherein the transparent polymeric material is a substantially transparent vision correction lens and is shaped to provide a predetermined vision-correcting optical power.

9. A method comprising:
transmitting an interrogation signal for receipt by an antenna of an eye-mountable device, wherein the antenna is disposed on a substrate at least partially embedded within a transparent polymeric material of the eye-mountable device, and wherein the eye-mountable device includes a sensor;
receiving, from the eye-mountable device, a response signal indicative of a substantially unique identification sequence, wherein the substantially unique identification sequence is based on process variations in components of a sequence generator of the eye-mountable device;
associating the eye-mountable device with device-specific information, wherein the device-specific information is a response to the substantially unique identification sequence received from the eye-mountable device and the device-specific information comprises user-specific information for operating the eye-mountable device; and
causing the eye-mountable device to operate the sensor in accordance with the user-specific information.

10. The method according to claim 9, wherein the associating includes querying a database to determine configuration information for the eye-mountable device.

11. The method according to claim 10, wherein the determined configuration information of the database includes calibration information specific to the of the eye-mountable device.

12. The method according to claim 11, wherein the calibration information is based on at least a previously obtained calibration result of the eye-mountable device.

13. The method according to claim 11, wherein the sensor is an electrochemical analyte sensor, the method further comprising:
determining an analyte concentration corresponding to a sensor measurement from the electrochemical analyte sensor based on the calibration information.

14. The method according to claim 9, wherein the associating includes querying a database to identify a particular user of the eye-mountable device.

15. The method according to claim 14, further comprising determining historical usage data for the identified particular user of the eye-mountable device.

16. The method according to claim 9, wherein the sensor is an electrochemical analyte sensor, the method further comprising:
wirelessly communicating with the eye-mountable device to obtain a measurement from the electrochemical analyte sensor included in the eye-mountable device; and
storing data indicative of the measurement in a database such that the stored data is associated with the substantially unique identification sequence.

17. A non-transitory computer readable medium storing instructions that, when executed by one or more processors in a computing device, cause the computing device to perform operations, the operations comprising:
transmitting an interrogation signal for receipt by an antenna of an eye-mountable device, wherein the antenna is disposed on a substrate at least partially embedded within a transparent polymeric material of the eye-mountable device, and wherein the eye-mountable device includes a sensor;
receiving, from the eye-mountable device, a response signal indicative of a substantially unique identification sequence, wherein the substantially unique identification sequence is based on process variations in components of a sequence generator of the eye-mountable device;
associating the eye-mountable device with device-specific information, wherein the device-specific information is a response to the substantially unique identification sequence received from the eye-mountable device and the device-specific information comprises user-specific information for operating the eye-mountable device; and
causing the eye-mountable device to operate the sensor in accordance with the user-specific information.

18. The non-transitory computer readable medium according to claim 17, wherein the associating includes querying a database to determine configuration information for the eye-mountable device.

19. A body-mountable device comprising:
a bio-compatible polymeric material;
a substrate at least partially embedded within the bio-compatible polymeric material;
an antenna disposed on the substrate;
a sensor;

a sequence generator that dynamically generates a substantially unique identification sequence, wherein the substantially unique identification sequence is based on process variations in components of the sequence generator; and a controller electrically connected to the antenna, wherein the controller: (i) receives an indication of an interrogation signal via the antenna, (ii) responsive to the interrogation signal, outputs the substantially unique identification sequence, (iii) uses the antenna to communicate the substantially unique identification sequence, (iv) responsive to communicating the substantially unique identification sequence, uses the antenna to receive an indication of device-specific information associated with the body-mountable device, wherein the device-specific information is a response to said communicating of the substantially unique identification sequence and the device-specific information comprises user-specific information for operating the body-mountable device, and (v) operates the sensor in accordance with the user-specific information.

20. The body-mountable device according to claim 19, wherein the sensor is an electrochemical sensor disposed on the substrate and including: (i) a working electrode, and (ii) a reference electrode adjacent the working electrode, and wherein the controller: (i) applies a voltage between the working electrode and the reference electrode sufficient to generate an amperometric current related to a concentration of an analyte in a fluid to which the body-mountable device is exposed, (ii) measures the amperometric current, and (iii) uses the antenna to indicate the measured amperometric current.

21. The body-mountable device according to claim 19, wherein the bio-compatible polymeric material mounts to a tooth surface such that the body-mountable device is a tooth-mountable device.

22. The body-mountable device according to claim 19, wherein the bio-compatible polymeric material mounts to a skin surface such that the body-mountable device is a skin-mountable device.

* * * * *